US010167298B2

(12) United States Patent
McNevin et al.

(10) Patent No.: US 10,167,298 B2
(45) Date of Patent: Jan. 1, 2019

(54) PSEUDOPOLYMORPHS OF AN HCV NS5A INHIBITOR AND USES THEREOF

(71) Applicant: MERCK SHARP & DOHME CORP., Rahway, NJ (US)

(72) Inventors: Michael McNevin, Basking Ridge, NJ (US); Yong Liu, Princeton, NJ (US); Ian Mangion, Cranford, NJ (US); Alfred Lee, Robbinsville, NJ (US); Joyce Stellabott, Perkasie, PA (US); Benjamin D. Sherry, New York, NY (US); Gary Martin, Warren Township, NJ (US); Kung-I Feng, Basking Ridge, NJ (US); Scott Schultz, Maplewood, NJ (US); Ryan Cohen, Piscataway, NJ (US); Yanfeng Zhang, Suzhou (CN)

(73) Assignee: Merck Sharp & Dohme Corp., Rahway, NJ (US)

( * ) Notice: Subject to any disclaimer, the term of this patent is extended or adjusted under 35 U.S.C. 154(b) by 0 days.

(21) Appl. No.: 15/032,663

(22) PCT Filed: Oct. 24, 2014

(86) PCT No.: PCT/US2014/062085
§ 371 (c)(1),
(2) Date: Apr. 28, 2016

(87) PCT Pub. No.: WO2015/065817
PCT Pub. Date: May 7, 2015

(65) Prior Publication Data
US 2016/0311834 A1 Oct. 27, 2016

Related U.S. Application Data

(60) Provisional application No. 61/897,552, filed on Oct. 30, 2013.

(51) Int. Cl.
*A61K 31/5365* (2006.01)
*C07D 498/04* (2006.01)
*A61P 1/16* (2006.01)
*A61K 45/06* (2006.01)

(52) U.S. Cl.
CPC ........ *C07D 498/04* (2013.01); *A61K 31/5365* (2013.01); *A61K 45/06* (2013.01); *A61P 1/16* (2018.01)

(58) Field of Classification Search
CPC ............................ A61K 31/5365; C07D 498/04
See application file for complete search history.

(56) References Cited

U.S. PATENT DOCUMENTS

| | | |
|---|---|---|
| 4,634,697 A | 1/1987 | Hamashima |
| 4,812,561 A | 3/1989 | Hamashima et al. |
| 4,933,443 A | 6/1990 | Hamashima et al. |
| 5,017,380 A | 5/1991 | Hamashima et al. |
| 6,767,991 B1 | 7/2004 | Llinas-Brunet et al. |
| 6,800,434 B2 | 10/2004 | Saksena et al. |
| 6,838,475 B2 | 1/2005 | Arasappan et al. |
| 6,846,802 B2 | 1/2005 | Chen et al. |
| 6,894,072 B2 | 5/2005 | Arasappan et al. |
| 6,911,428 B2 | 6/2005 | Zhu et al. |
| 6,914,122 B2 | 7/2005 | Venkatraman et al. |
| 7,012,066 B2 | 3/2006 | Saksena et al. |
| 7,169,760 B2 | 1/2007 | Saksena et al. |
| 7,173,057 B2 | 2/2007 | Chen et al. |
| 7,186,747 B2 | 3/2007 | Arasappan et al. |
| 7,192,957 B2 | 3/2007 | Venkatraman et al. |
| 7,205,330 B2 | 4/2007 | Bogen et al. |
| 7,244,721 B2 | 7/2007 | Saksena et al. |
| 7,253,160 B2 | 8/2007 | Njoroge et al. |
| 7,273,885 B2 | 9/2007 | Pitlik et al. |
| 7,342,041 B2 | 3/2008 | Njoroge et al. |
| 7,425,576 B2 | 9/2008 | Arasappan et al. |
| 7,442,695 B2 | 10/2008 | Njoroge et al. |
| 7,449,447 B2 | 11/2008 | Chen et al. |
| 7,485,625 B2 | 2/2009 | Velazquez et al. |
| 7,494,988 B2 | 2/2009 | Perni et al. |
| 8,871,759 B2 * | 10/2014 | Coburn ................ C07D 401/14 514/229.5 |
| 2002/0068702 A1 | 6/2002 | Lim-Wilby et al. |
| 2002/0160962 A1 | 10/2002 | Saksena et al. |
| 2005/0119168 A1 | 6/2005 | Venkatraman et al. |

(Continued)

FOREIGN PATENT DOCUMENTS

| | | |
|---|---|---|
| WO | 199814181 A1 | 4/1998 |
| WO | 199817679 A1 | 4/1998 |

(Continued)

OTHER PUBLICATIONS

Beaulieu., et al., "Inhibitors of the HCV NS5B polymerase: New hope for the treatment of hepatitis C infections", Current Opinions in Investigational Drugs, 2004, p. 838. vol. 5.
Dismasi., et al., "Characterization of Engineered Hepatitis C Virus NS3 ProteaseInhibitors Affinity Selected from Human Pancreatic Secretory Trypsin Inhibitor and Minibody Repertoires"; Journal of Virology, 1997, pp. 7461-7469, vol. 71 No. 10.
Elzouki., et al., "Serine protease inhibitors in patients with chronic viral hepatitis", Journal of Hepatology, 1997, pp. 42-48, vol. 27.
Ingallinella., et al., "Potent Peptide Inhibitors of Human Hepatitis C Virus NS3 Protease Are Obtained by Optimizing the Cleavage Products", Biochemistry, 1998, pp. 8906-8914, vol. 37.

(Continued)

*Primary Examiner* — Theodore R. West
(74) *Attorney, Agent, or Firm* — Jeffrey P. Bergman; Catherine D. Fitch

(57) ABSTRACT

The present invention relates to novel Pseudopolymorphs of Compound A, compositions comprising at least one Pseudopolymorph of Compound A, and methods of using the Pseudopolymorphs of Compound A for preparing compositions useful for treating or preventing HCV infection in a patient, wherein Compound A has the structure.

17 Claims, 12 Drawing Sheets

(56) References Cited

U.S. PATENT DOCUMENTS

| | | | |
|---|---|---|---|
| 2005/0176648 A1 | 8/2005 | Saksena et al. | |
| 2005/0209164 A1 | 9/2005 | Bogen et al. | |
| 2005/0249702 A1 | 11/2005 | Njoroge et al. | |
| 2007/0042968 A1 | 2/2007 | Bennett et al. | |
| 2007/0274951 A1 | 11/2007 | Tong et al. | |
| 2008/0044379 A1 | 2/2008 | Bachand et al. | |
| 2008/0044380 A1 | 2/2008 | Bachand et al. | |
| 2008/0311075 A1 | 12/2008 | Bachand et al. | |
| 2009/0020478 A1 | 1/2009 | Erwe et al. | |
| 2009/0022688 A1 | 1/2009 | Farmer et al. | |
| 2009/0081636 A1 | 3/2009 | Huang | |
| 2009/0202483 A1 | 8/2009 | Bachand et al. | |
| 2012/0083483 A1 | 4/2012 | Coburn et al. | |

FOREIGN PATENT DOCUMENTS

| | | | | |
|---|---|---|---|---|
| WO | 199822496 A1 | 5/1998 | | |
| WO | 199907734 A1 | 2/1999 | | |
| WO | WO2003006490 | 1/2003 | | |
| WO | 2003087092 | 10/2003 | | |
| WO | 2004092161 | 10/2004 | | |
| WO | 2005087731 | 9/2005 | | |
| WO | 2006019832 A1 | 2/2006 | | |
| WO | 2008083351 | 7/2008 | | |
| WO | WO2008082484 | 7/2008 | | |
| WO | WO2008082488 | 7/2008 | | |
| WO | 2008124148 | 10/2008 | | |
| WO | 2008136815 | 11/2008 | | |
| WO | 2009032116 | 3/2009 | | |
| WO | 2009032123 | 3/2009 | | |
| WO | 2009032124 | 3/2009 | | |
| WO | 2009032125 | 3/2009 | | |
| WO | 2010065668 A1 | 6/2010 | | |
| WO | 2010065674 A1 | 6/2010 | | |
| WO | 2010065681 | 6/2010 | | |
| WO | 201011483 A1 | 9/2010 | | |
| WO | WO-2012040923 A1 * | 4/2012 | ........... | A61K 31/404 |
| WO | 201314214 A1 | 9/2013 | | |
| WO | 2013149981 A1 | 10/2013 | | |

OTHER PUBLICATIONS

Landro., et al., "Mechanistic Role of an NS4A Peptide Cofactor with the Truncated NS3 Protease of Hepatitis C Virus: Elucidatian of the NS4A Stimulatory Effect Via Kinetic Analysis and Inhibitor Mapping", Biochemistry, 1997, pp. 9340-9348, vol. 31.

Llinas-Brunet., et al., "Peptide-based Inhibitors of the Hepatitis C Virus Serine Protease", Bioorganic & Medicinal Chemistry Letters, 1998, pp. 1713-1718, vol. 8.

Gao, M., et al., "Chemical Genetics Strategy Identifies An HCV NS5A Inhibitor With A Patent Clinical Effect", Nature, 2010, pp. 96-100, vol. 465, US.

Martin., et al., "Affinity Selection of a Camelized VH Domain Antibody Inhibitor of Hepatitis C Virus NS3 Protease", Protein Engineering, 1997, pp. 607-614, vol. 10, No. t.

Martin., et al., "Design of selective Eglin Inhibitors of HCV NS3 Proteinase", Biochemistry, 1998, pp. 11459-11468, vol. 37, No. 33.

Ni., et al., "Progress and Development of Small Molecule HCV Antivirals", Current Opinion in Drug Discovery and Development, 2004, pp. 446, vol. 7, No. 4.

Tan., et al., "Hepatitis C Therapeutics Current and Emerging Strategies", Nature Reviews, 2002, pp. 887-831, vol. 1.

Huang, Y., et al, "Phosphorylation of Hepatitis C Virus NS5A Nonstructural Protein: A New Paradigm For Phosphorylation-Dependent Viral RNA Replicaton", Virology, 2007, pp. 1-9, vol. 364, US.

Tanji, Y., et al., "Phosphorylation of Hepatitis C Virus-Encloded Nonstructural Protein NS5A", Journal of Virology, 1995, pp. 3980-3986, vol. 69, No. 7, US.

Coburn, et al., Discovery of MK-8742: An HCV NS5A Inhibitor with Broad Genotype activity, ChemMedChem, 2013, pp. 1930-1940, vol. 8 No. 12.

Seddon, K. et al., Pseudopolymorph: A Polemic, Crystal Growth & Design, 2004, 1087, vol. 4, No. 6.

Supplementary Partial European Search Report for 14858933.6, dated May 24, 2017, 6 pages.

* cited by examiner

PSEUDOPOLYMORPHS OF AN HCV NS5A INHIBITOR AND USES THEREOF

CROSS-REFERENCE TO RELATED APPLICATIONS

This application is the national stage application under 35 U.S.C. 371 of International Patent Application No. PCT/US2014/062085, filed Oct. 24, 2014, which claims priority to U.S. Provisional Patent Application No. 61/897,552, filed Oct. 30, 2013. Each of the aforementioned PCT and provisional applications is incorporated by reference in its entirety.

FIELD OF THE INVENTION

The present invention relates to novel Pseudopolymorphs of Compound A, compositions comprising at least one Pseudopolymorph of Compound A, and methods of using the Pseudopolymorphs of Compound A for preparing compositions useful for treating or preventing HCV infection in a patient.

BACKGROUND OF THE INVENTION

HCV NS5A is a 447 amino acid phosphoprotein which lacks a defined enzymatic function. It runs as 56 kd and 58 kd bands on gels depending on phosphorylation state (Tanji, et al. *J. Virol.* 69:3980-3986 (1995)). HCV NS5A resides in replication complex and may be responsible for the switch from replication of RNA to production of infectious virus (Huang, Y, et al., *Virology* 364:1-9 (2007)).

Multicyclic HCV NS5A inhibitors have been reported. See U.S. Patent Publication Nos. US20080311075, 0520080044379, US20080050336, US20080044380, US20090202483 and US2009020478. HCV NS5A inhibitors having fused tricyclic moieties are disclosed in International Patent Publication Nos. WO 10/065681, WO 10/065668, and WO 10/065674.

Other HCV NS5A inhibitors and their use for reducing viral load in HCV infected humans have been described in U.S. Patent Publication No. US20060276511.

The compound dimethyl((2S,2'S)-((2S,2'S)-2,2'-(5,5'-(6-phenyl-6H benzo[5,6][1,3]oxazino[3,4-a]indole-3,10-diyl)bis(1H-imidazole-5,2-diyl))bis(pyrrolidine-2,1-diyl)bis(3-methyl-1-oxobutane-2,1-diyl))dicarbamate (hereinafter designated as "Compound A") is a potent HCV NS5A inhibitor. The structure of Compound A is as follows:

Compound A

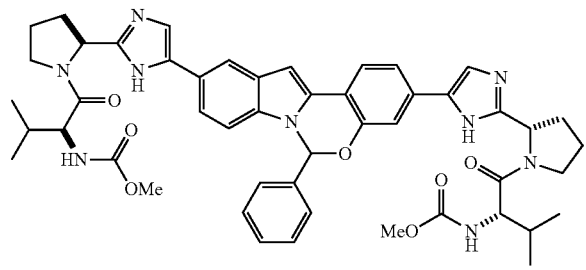

Compound A is disclosed in US Patent Publication No. US20120083483.

SUMMARY OF THE INVENTION

In one aspect, the present invention provides Pseudopolymorphs of Compound A:

Compound A

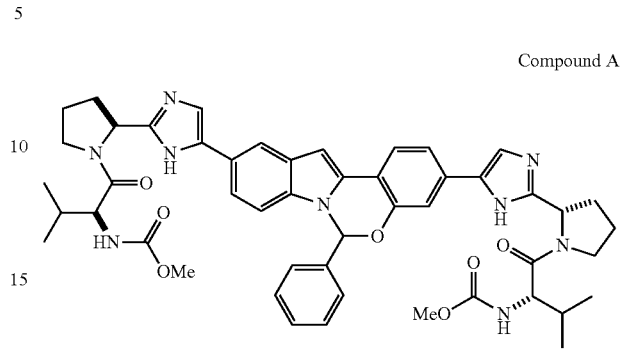

Compound A can be useful, for example, for inhibiting HCV viral replication or replicon activity, for treating or preventing HCV infection in a patient, and for preparing amorphous dosage forms. Without being bound by any specific theory, it is believed that Compound A inhibits HCV viral replication by inhibiting HCV NS5A.

Accordingly, in one aspect, the present invention provides methods for treating or preventing HCV infection in a patient, comprising administering to the patient an effective amount of Compound A.

In another aspect, the present invention provides pharmaceutical compositions comprising:

(1) Compound A, or a pharmaceutically acceptable salt thereof;

(2) a concentration-enhancing polymer, where the polymer increases the bioavailability or enhances the dissolution behavior of Compound A, and is water soluble or readily disperses in water; and (3) optionally one or more surfactants.

In another aspect, the present invention provides compositions comprising Compound A, wherein said compositions are made by a process selected from: (1) spray drying of a solution comprising a pseudopolymorph of Compound A or a pharmaceutically acceptable salt thereof, the concentration-enhancing polymer, the optional one or more surfactants, and one or more solvents; and (2) hot melt extrusion of a mixture comprising a pseudopolymorph of Compound A or a pharmaceutically acceptable salt thereof, the concentration-enhancing polymer, and the optional one or more surfactants.

In still another aspect, the present invention provides a method for making compostions comprising Compound A, wherein said method comprises the steps: (a) rendering a pseudopolymorph of Compound A amorphous; and (b) putting a pharmaceutically effective amount of the amorphous form of Compound A into a dosage form.

The details of the invention are set forth in the accompanying detailed description below.

Although any methods and materials similar to those described herein can be used in the practice or testing of the present invention, illustrative methods and materials are now described. Other embodiments, aspects and features of the present invention are either further described in or will be apparent from the ensuing description, examples and appended claims.

DETAILED DESCRIPTION OF THE INVENTION

Figure 1:
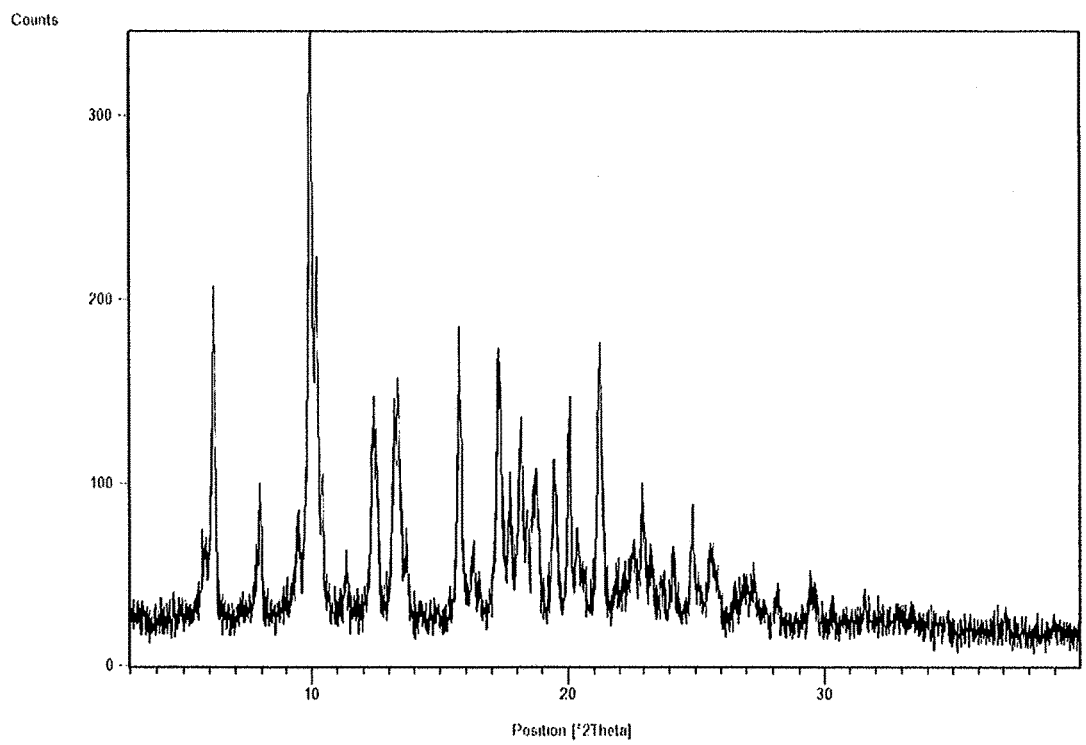
FIG. 1 shows the powder x-ray diffraction (XRPD) pattern of form A of Compound A (methanolate).

The present invention relates to novel Pseudopolymorphs of Compound A, compositions comprising at least one Pseudopolymorph of Compound A, and methods of using the Pseudopolymorphs of Compound A for treating or preventing HCV infection in a patient.

Definitions and Abbreviations

The terms used herein have their ordinary meaning and the meaning of such terms is independent at each occurrence thereof. That notwithstanding and except where stated otherwise, the following definitions apply throughout the specification and claims. Chemical names, common names, and chemical structures may be used interchangeably to describe the same structure. If a chemical compound is referred to using both a chemical structure and a chemical name and an ambiguity exists between the structure and the name, the structure predominates. These definitions apply regardless of whether a term is used by itself or in combination with other terms, unless otherwise indicated.

As used herein, and throughout this disclosure, the following terms, unless otherwise indicated, shall be understood to have the following meanings.

The term "anhydrous form" refers to a particular form essentially free of water.

The term "amorphous form" refers to a chemically and physically stable amorphous, non-crystalline form of Compound A.

The term "pseudopolymorph" as used herein, refers to a form of a chemical structure. "Pseudopolymorphs" of Compound A, according to the present invention include, but are not limited to, crystalline forms, anhydrous forms, hydrates, salts and solvates of Compound A.

A "patient" is a human or non-human mammal. In one embodiment, a patient is a human. In another embodiment, a patient is a chimpanzee.

The term "dosage form" refers to a pharmaceutical products comprising Compound A, wherein the pharmaceutical product is in the form suitable for administration. The dosage form comprises a mixture of active drug component(s) and nondrug component(s) (excipient(s)), along with other non-reusable material that may not be considered either ingredient or packaging (such as a capsule shell, for example). The term "dosage form" also refers to a chemical formulation comprising Compound A and any blends involved, without considering its ultimate configuration as a consumable product such as a tablet or capsule. Depending on the method/route of administration, a dosage forms may exist in several types. These include, but are not limited to, liquid, solid, and semisolid dosage forms. Non-limiting dosage forms include pills, tablets, capsules, suspensions, drinks or syrups. A dosage form can be administered various ways, including orally and intravenously.

The term "effective amount" as used herein, refers to an amount of Compound A and/or an additional therapeutic agent, or a composition thereof that is effective in inhibiting HCV replication and preferably in producing the desired therapeutic, ameliorative, inhibitory or preventative effect when administered to a patient suffering from a viral infection or virus-related disorder. In the combination therapies of the present invention, an effective amount can refer to each individual agent or to the combination as a whole, wherein the amounts of all agents administered are together effective.

The term "preventing," as used herein with respect to an HCV viral infection or HCV-virus related disorder, refers to reducing the likelihood of HCV infection.

The term "in substantially purified form," as used herein, refers to the physical state of a compound after the compound is isolated from a synthetic process (e.g., from a reaction mixture), a natural source, or a combination thereof. The term "in substantially purified form," also refers to the physical state of a compound after the compound is obtained from a purification process or processes described herein or well-known to the skilled artisan (e.g., chromatography, recrystallization and the like), in sufficient purity to be characterizable by standard analytical techniques described herein or well-known to the skilled artisan.

It should also be noted that any carbon as well as heteroatom with unsatisfied valences in the text, schemes, examples and tables herein is assumed to have the sufficient number of hydrogen atom(s) to satisfy the valences.

When a functional group in a compound is termed "protected", this means that the group is in modified form to preclude undesired side reactions at the protected site when the compound is subjected to a reaction. Suitable protecting groups will be recognized by those with ordinary skill in the art as well as by reference to standard textbooks such as, for example, T. W. Greene et al, *Protective Groups in Organic Synthesis* (1991), Wiley, New York.

As used herein, the term "composition" is intended to encompass a product comprising the specified ingredients in the specified amounts, as well as any product which results from combination of the specified ingredients in the specified amounts.

The term "$C_1$-$C_4$ alcohol" defines straight and/or branched chained saturated and unsaturated hydrocarbons having from 1 to 4 carbon atoms substituted with at least a hydroxyl group, and optionally substituted with an alkyloxy group, such as, for example, methanol, ethanol, isopropanol, butanol, 1-methoxy-2-propanol and the like.

The term "$C_2$-$C_4$ glycol" defines saturated hydrocarbons having from 2 to 4 carbon atoms, and substituted with 2 hydroxyl groups, such as, for example, ethylene glycol, propylene glycol, and the like.

The term "$C_1$-$C_4$ chloroalkane" defines straight and/or branched chained saturated and unsaturated hydrocarbons having from 1 to 4 carbon atoms substituted with at least one chloro atom, such as, for example, dichloromethane.

The term "$C_1$-$C_5$ ketone" defines solvents of the general formula R'—C(=O)—R wherein R and R' can be the same or different and are methyl or ethyl, such as, acetone and the like.

The term "$C_1$-$C_4$ ether" defines solvents of the general formula R'—O—R wherein R and R' can be the same or different and are a phenyl group, methyl or ethyl, such as, anisole and the like.

The term "cycloether" defines a 4- to 6-membered monocyclic hydrocarbons containing one or two oxygen ring atoms, such as tetrahydrofuran and the like.

The term "$C_1$-$C_5$ ester" defines solvents of the general formula R'—O—C(=O)—R wherein R and R' can be the same or different and are methyl or ethyl, such as ethylacetate and the like.

A Pseudopolymorph of Compound A may be a solvate. Preparation of solvates is generally known. "Solvate" means a physical association of Compound A with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. "Solvate" encompasses both solution-phase and isolatable solvates. Non-limiting examples of solvates include ethanolates, methanolates, ethanolates, and the like. Thus, for example, M. Caira et al, *J. Pharmaceutical Sci.*, 93(3), 601-611 (2004) describe the preparation of the solvates of the antifungal fluconazole in ethyl acetate as well as from water. Similar preparations of solvates, hemisolvate, hydrates and the like are described by E. C. van Tonder et al, *AAPS PharmSciTechours.*, 5(1), article 12 (2004); and A. L. Bingham et al, *Chem. Commun.*, 603-604 (2001). A typical, non-limiting, process involves dissolving the inventive compound in desired amounts of the desired solvent (organic or water or mixtures thereof) at a higher than room temperature, and cooling the solution at a rate sufficient to form crystals which are then isolated by standard methods. Analytical techniques such as, for example IR spectroscopy, show the presence of the solvent (or water) in the crystals as a solvate (or hydrate). Accordingly, one or more Pseudopolymorphs of Compound A may exist in unsolvated as well as solvated forms with pharmaceutically acceptable solvents, and it is intended that the invention embrace both solvated and unsolvated forms. A "hydrate" is a solvate wherein the solvent molecule is water. Solvates can occur in different ratios of solvation. Solvent content of the crystal may vary in different ratios depending on the conditions applied. Solvate crystal forms of Compound A may comprise multiple molecules of solvent per molecule of Compound A appearing in different solvated states including, amongst others, hemisolvate, monosolvate, disolvate, trisolvate crystals, intermediate solvates crystals, and mixtures thereof.

Solvates may also occur at different levels of hydration. As such, solvate crystal forms of Compound A may additionally comprise water molecules partially or fully in the crystal structures.

The Pseudopolymorphs of Compound A can exist as salts which are also within the scope of this invention. Reference to a Pseudopolymorph of Compound A herein is understood to include, in the alternative, reference to salts thereof, unless otherwise indicated. The term "salt(s)", as employed herein, denotes acidic salts formed with inorganic and/or organic acids, as well as basic salts formed with inorganic and/or organic bases. In addition, when a Pseudopolymorph of Compound A contains both a basic moiety, such as, but not limited to a pyridine or imidazole, and an acidic moiety, such as, but not limited to a carboxylic acid, zwitterions ("inner salts") may be formed and are included within the term "salt(s)" as used herein. In one embodiment, the salt is a pharmaceutically acceptable (i.e., non-toxic, physiologically acceptable) salt. In another embodiment, the salt is other than a pharmaceutically acceptable salt. Salts of Compound A may be formed, for example, by reacting Compound A with an amount of acid or base, such as an equivalent amount, in a medium such as one in which the salt precipitates or in an aqueous medium followed by lyophilization.

Exemplary acid addition salts include acetates, ascorbates, benzoates, benzenesulfonates, bisulfates, borates, butyrates, citrates, camphorates, camphorsulfonates, fumarates, hydrochlorides, hydrobromides, hydroiodides, lactates, maleates, methanesulfonates, naphthalenesulfonates, nitrates, oxalates, phosphates, propionates, salicylates, succinates, sulfates, tartarates, thiocyanates, toluenesulfonates (also known as tosylates) and the like. Additionally, acids which are generally considered suitable for the formation of pharmaceutically useful salts from basic pharmaceutical compounds are discussed, for example, by P. Stahl et al, Camille G. (eds.) *Handbook of Pharmaceutical Salts. Properties, Selection and Use*. (2002) Zurich: Wiley-VCH; S. Berge et al, *Journal of Pharmaceutical Sciences* (1977) 66(1) 1-19; P. Gould, *International J. of Pharmaceutics* (1986) 33 201-217; Anderson et al, *The Practice of Medicinal Chemistry* (1996), Academic Press, New York; and in *The Orange Book* (Food & Drug Administration, Washington, D.C. on their website). These disclosures are incorporated herein by reference thereto.

Exemplary basic salts include ammonium salts, alkali metal salts such as sodium, lithium, and potassium salts, alkaline earth metal salts such as calcium and magnesium salts, salts with organic bases (for example, organic amines) such as dicyclohexylamine, t-butyl amine, choline, and salts with amino acids such as arginine, lysine and the like. Basic nitrogen-containing groups may be quarternized with agents such as lower alkyl halides (e.g., methyl, ethyl, and butyl chlorides, bromides and iodides), dialkyl sulfates (e.g., dimethyl, diethyl, and dibutyl sulfates), long chain halides (e.g., decyl, lauryl, and stearyl chlorides, bromides and iodides), aralkyl halides (e.g., benzyl and phenethyl bromides), and others.

Diastereomeric mixtures can be separated into their individual diastereomers on the basis of their physical chemical differences by methods well-known to those skilled in the art, such as, for example, by chromatography and/or fractional crystallization. Enantiomers can be separated by converting the enantiomeric mixture into a diastereomeric mixture by reaction with an appropriate optically active compound (e.g., chiral auxiliary such as a chiral alcohol or Mosher's acid chloride), separating the diastereomers and converting (e.g., hydrolyzing) the individual diastereomers to the corresponding pure enantiomers. Sterochemically pure compounds may also be prepared by using chiral starting materials or by employing salt resolution techniques. Also, some of the Pseudopolymorphs of Compound A may be atropisomers (e.g., substituted biaryls) and are considered as part of this invention. Enantiomers can also be directly separated using chiral chromatographic techniques.

It is also possible that the Pseudopolymorphs of Compound A may exist in different tautomeric forms, and all such forms are embraced within the scope of the invention. For example, all keto-enol and imine-enamine forms of the compounds are included in the invention.

All stereoisomers (for example, geometric isomers, optical isomers and the like) of the present compounds (including those of the salts, solvates, hydrates and esters of the compounds), such as those which may exist due to asymmetric carbons on various substituents, including enantiomeric forms (which may exist even in the absence of asymmetric carbons), rotameric forms, atropisomers, and diastereomeric forms, are contemplated within the scope of this invention. If a Pseudopolymorph of Compound A incorporates a double bond or a fused ring, both the cis- and trans-forms, as well as mixtures, are embraced within the scope of the invention.

Individual stereoisomers of Pseudopolymorphs of Compound A may, for example, be substantially free of other isomers, or may be admixed, for example, as racemates or with all other, or other selected, stereoisomers. The chiral centers of the present invention can have the S or R configuration as defined by the IUPAC 1974 Recommendations. The use of the terms "salt", "solvate", "ester" and the like, is intended to apply equally to the salt, solvate, ester of enantiomers, stereoisomers, rotamers, tautomers or racemates of the inventive compounds.

In the Pseudopolymorphs of Compound A, the atoms may exhibit their natural isotopic abundances, or one or more of the atoms may be artificially enriched in a particular isotope having the same atomic number, but an atomic mass or mass number different from the atomic mass or mass number predominantly found in nature. The present invention is meant to include all suitable isotopic variations of the compounds of generic Formula I. For example, different isotopic forms of hydrogen (H) include protium ($^1$H) and deuterium ($^2$H). Protium is the predominant hydrogen isotope found in nature. Enriching for deuterium may afford certain therapeutic advantages, such as increasing in vivo half-life or reducing dosage requirements, or may provide a compound useful as a standard for characterization of biological samples. Isotopically-enriched Pseudopolymorphs of Compound A can be prepared without undue experimentation by conventional techniques well known to those skilled in the art or by processes analogous to those described in the Schemes and Examples herein using appropriate isotopically-enriched reagents and/or intermediates.

The Pseudopolymorphs of Compound A

The present invention provides Pseudopolymorphs of Compound A:

(I)

In one embodiment, Compound A is in amorphous form.

In another embodiment, the pseudopolymorph is a pharmaceutically acceptable salt of Compound A.

In one embodiment, the pseudopolymorph of Compound A is a solvate of Compound A.

In another embodiment, the pseudopolymorph of Compound A is a hydrate, alcohol solvate, chloroalkane solvate, ester solvate, cycloether solvate, glycol solvate or ketone solvate.

In another embodiment, the pseudopolymorph of Compound A is a hydrate, alcohol solvate, glycol solvate or ketone solvate.

In still another embodiment, the pseudopolymorph of Compound A is a hydrate, alcohol solvate, glycol solvate or ketone solvate.

In another embodiment, the pseudopolymorph of Compound A is a hydrate, a $C_1$-$C_4$ alcohol solvate, a $C_2$-$C_4$ glycol solvate or a $C_1$-$C_5$ ketone solvate.

In one embodiment the pseudopolymorph of Compound A is a glycol solvate of Compound A. In another embodiment the pseudopolymorph of Compound A is a $C_1$-$C_5$ ketone solvate of Compound A.

In still another embodiment, the pseudopolymorph of Compound A is a mixed solvate.

In another embodiment, the pseudopolymorph of Compound A is pharmaceutically acceptable.

In one embodiment, the pseudopolymorph of Compound A is a solvate selected from Form A (methanolate), Form B (ethanolate), Form C (1-propanolate), Form D (2-propanolate), Form E (acetonate), Form F (1-butanolate), Form G (ethylene glycolate), Form H (propylene glycolate), Form I (methyl isobutyl ketone/propylene glycol mixed solvate), Form J (hydrate) and Form K (1,5-naphthalene disulfonic acid salt methanol solvate).

In another embodiment, the pseudopolymorph of Compound A is a solvate selected from Form A (methanolate), Form B (ethanolate), Form C (1-propanolate), Form D (2-propanolate), Form E (acetonate), Form F (1-butanolate), Form G (ethylene glycolate), Form H (propylene glycolate), Form I (methyl isobutyl ketone/propylene glycol mixed solvate) and Form J (hydrate).

In one embodiment, the pseudopolymorph of Compound A is a methanol solvate.

In another embodiment, the pseudopolymorph of Compound A is an ethanol solvate.

In another embodiment, the pseudopolymorph of Compound A is a 1-propanol solvate.

In still another embodiment, the pseudopolymorph of Compound A is 2-propanol solvate.

In another embodiment, the pseudopolymorph of Compound A is an acetone solvate.

In another embodiment, the pseudopolymorph of Compound A is an ethylene glycol solvate.

In yet another embodiment, the pseudopolymorph of Compound A is a propylene glycol solvate.

In another embodiment, the pseudopolymorph of Compound A is a methyl isobutyl ketone/propylene glycol mixed solvate.

In another embodiment the pseudopolymorph of Compound A is a hydrate of Compound A.

In a further embodiment, the pseudopolymorph of Compound A is a 1-propanol solvate.

In another embodiment, the pseudopolymorph of Compound A is a 1,5-Napthalene Disulfonic Acid Salt Methanol Solvate.

In one embodiment, the pseudopolymorph of Compound A is in crystalline form.

In another embodiment, the pseudopolymorph of Compound A is a crystalline methanol solvate, having an X-ray powder diffraction (XRPD) pattern comprising diffraction peaks at 2-theta values, when measured using Cu K$_\alpha$ radiation, of about 6.19±0.2, 10.10±0.2, 15.76±0.2, 17.27±0.2 and 21.24±0.2.

In another embodiment, the pseudopolymorph of Compound A is a crystalline ethanol solvate, having an X-ray powder diffraction pattern comprising diffraction peaks at 2-theta values, when measured using Cu K$_\alpha$ radiation, of about 6.13±0.2, 10.05±0.2, 13.30±0.2, 15.66±0.2 and 17.53±0.2.

In still another embodiment, the pseudopolymorph of Compound A is a crystalline 1-propanolate solvate, having an X-ray powder diffraction pattern comprising diffraction peaks at 2-theta values, when measured using Cu K$_\alpha$ radiation, of about 6.23±0.2, 10.16±0.2, 12.49±0.2, 18.37±0.2 and 19.62±0.2.

In another embodiment, the pseudopolymorph of Compound A is a crystalline 2-propanol solvate having an X-ray powder diffraction pattern comprising diffraction peaks at 2-theta values, when measured using Cu K$_\alpha$ radiation, of about 6.12±0.2, 10.03±0.2, 13.38±0.2, 17.57±0.2 and 18.33±0.2.

In another embodiment, the pseudopolymorph of Compound A is a crystalline acetone solvate, having an X-ray powder diffraction pattern comprising diffraction peaks at 2-theta values, when measured using Cu K$_\alpha$ radiation, of about 5.92±0.2, 8.52±0.2, 11.97±0.2, 17.07±0.2 and 20.39±0.2.

In yet another embodiment, the pseudopolymorph of Compound A is a crystalline 1-butanol solvate, having an X-ray powder diffraction pattern comprising diffraction peaks at 2-theta values, when measured using Cu K$_\alpha$ radiation, of about 5.68±0.2, 9.88±0.2, 11.69±0.2, 18.38±0.2 and 19.29±0.2.

In another embodiment, the pseudopolymorph of Compound A is a crystalline ethylene glycol solvate, having an X-ray powder diffraction pattern comprising diffraction peaks at 2-theta values, when measured using Cu K$_\alpha$ radiation, of about 9.87±0.2, 13.08±0.2, 17.23±0.2, 19.86±0.2 and 20.93±0.2.

In a further embodiment, the pseudopolymorph of Compound A is a crystalline propylene glycol solvate, having an X-ray powder diffraction pattern comprising diffraction peaks at 2-theta values, when measured using Cu K$_\alpha$ radiation, of about 6.08±0.2, 9.99±0.2, 13.28±0.2, 15.64±0.2 and 17.43±0.2.

In another embodiment, the pseudopolymorph of Compound A is a crystalline methyl isobutyl ketone/propylene glycol mixed solvate, having an X-ray powder diffraction pattern comprising diffraction peaks at 2-theta values, when measured using Cu K$_\alpha$ radiation, of about 4.89±0.2, 5.74±0.2, 11.82±0.2, 18.66±0.2 and 19.42±0.2.

In another embodiment, the pseudopolymorph of Compound A is a crystalline hydrate, having an X-ray powder diffraction pattern comprising diffraction peaks at 2-theta values, when measured using Cu K$_\alpha$ radiation, of about 6.31±0.2, 10.01±0.2, 10.34±0.2, 12.54±0.2 and 17.39±0.2.

In yet another embodiment, the pseudopolymorph of Compound A is a 1,5-napthalene disulfonic acid salt of Compound A.

In another embodiment, the pseudopolymorph of Compound A is the crystalline methanol solvate of a 1,5-napthalene disulfonic acid salt, having an X-ray powder diffraction pattern comprising diffraction peaks at 2-theta values, when measured using Cu K$_\alpha$ radiation, of about 15.16±0.2, 18.77±0.2, 19.43±0.2, 23.11±0.2 and 24.34±0.2.

In one embodiment, the pseudopolymorph of Compound A is a crystalline methanol solvate, having an X-ray powder diffraction pattern comprising diffraction peaks at 2-theta values, when measured using Cu K$_\alpha$ radiation, of about 6.29±0.2, 7.90±0.2, 11.89±0.2, 14.78±0.2, 15.16±0.2, 18.27±0.2, 18.77±0.2, 19.43±0.2, 24.34±0.2 and 26.02±0.2.

In another embodiment, the pseudopolymorph of Compound A is a crystalline ethanol solvate, having an X-ray powder diffraction pattern comprising diffraction peaks at 2-theta values, when measured using Cu K$_\alpha$ radiation, of about 6.13±0.2, 7.86±0.2, 9.59±0.2, 10.05±0.2, 12.37±0.2, 13.30±0.2, 15.66±0.2, 17.53±0.2, 18.28±0.2, and 20.06±0.2.

In still another embodiment, the pseudopolymorph of Compound A is a crystalline 1-propanol solvate, having an X-ray powder diffraction pattern comprising diffraction peaks at 2-theta values, when measured using Cu K$_\alpha$ radiation, of about 6.23±0.2, 7.97±0.2, 10.16±0.2, 12.49±0.2, 13.39±0.2, 15.88±0.2, 17.58±0.2, 18.37±0.2, 19.62±0.2 and 21.39±0.2.

In another embodiment, the pseudopolymorph of Compound A is a crystalline 2-propanol solvate having an X-ray powder diffraction pattern comprising diffraction peaks at 2-theta values, when measured using Cu K$_\alpha$ radiation, of about 6.12±0.2, 10.03±0.2, 12.36±0.2, 13.38±0.2, 15.76±0.2, 17.57±0.2, 18.33±0.2 18.98±0.2, 20.14±0.2, and 21.25±0.2.

In another embodiment, the pseudopolymorph of Compound A is a crystalline acetone solvate, having an X-ray powder diffraction pattern comprising diffraction peaks at 2-theta values, when measured using Cu K$_\alpha$ radiation, of about 5.92±0.2, 8.52±0.2, 9.78±0.2, 11.97±0.2, 15.22±0.2, 17.07±0.2, 17.89±0.2, 19.13±0.2, 20.39±0.2 and 21.66±0.2.

In yet another embodiment, the pseudopolymorph of Compound A is a crystalline 1-butanol solvate, having an X-ray powder diffraction pattern comprising diffraction peaks at 2-theta values, when measured using Cu K$_\alpha$ radiation, of about 5.68±0.2, 9.88±0.2, 11.69±0.2, 13.03±0.2, 15.32±0.2, 17.33±0.2, 18.38±0.2, 19.29±0.2, 19.98±0.2 and 21.04±0.2.

In another embodiment, the pseudopolymorph of Compound A is a crystalline ethylene glycol solvate, having an X-ray powder diffraction pattern comprising diffraction peaks at 2-theta values, when measured using Cu K$_\alpha$ radiation, of about 9.87±0.2, 13.08±0.2, 17.23±0.2, 18.06±0.2, 18.58±0.2, 19.30±0.2, 19.86±0.2, 20.93±0.2, 22.42±0.2 and 24.53±0.2.

In a further embodiment, the pseudopolymorph of Compound A is a crystalline 1-propanol solvate propylene glycol solvate, having an X-ray powder diffraction pattern comprising diffraction peaks at 2-theta values, when measured using Cu K$_\alpha$ radiation, of about 6.08±0.2, 9.99±0.2, 10.19±0.2, 10.35±0.2, 12.32±0.2, 13.28±0.2, 15.64±0.2, 17.43±0.2, 19.52±0.2 and 21.20±0.2.

In another embodiment, the pseudopolymorph of Compound A is a crystalline methyl isobutyl ketone/propylene glycol mixed solvate, having an X-ray powder diffraction pattern comprising diffraction peaks at 2-theta values, when measured using Cu K$_\alpha$ radiation, of about 4.89±0.2, 5.74±0.2, 10.07±0.2, 11.82±0.2, 13.14±0.2, 17.28±0.2, 18.66±0.2, 19.03±0.2, 19.42±0.2 and 21.61±0.2.

In another embodiment, the pseudopolymorph of Compound A is a crystalline hydrate, having an X-ray powder diffraction pattern comprising diffraction peaks at 2-theta values, when measured using Cu K$_\alpha$ radiation, of about 6.31±0.2, 10.01±0.2, 10.34±0.2, 12.54±0.2, 13.50±0.2, 16.00±0.2, 17.39±0.2, 18.29±0.2, 20.01±0.2 and 21.46±0.2.

In another embodiment, the pseudopolymorph of Compound A is the crystalline methanol solvate of the 1,5-napthalene disulfonic acid salt of Compound A, having an X-ray powder diffraction pattern comprising diffraction peaks at 2-theta values, when measured using Cu K$_\alpha$ radiation, of about 7.90±0.2, 11.89±0.2, 15.16±0.2, 18.27±0.2, 18.77±0.2, 19.43±0.2, 23.11±0.2, 23.75±0.2, 24.34±0.2 and 24.77±0.2. In a further embodiment, the pseudopolymorph of Compound A is a crystalline methanol solvate, having an X-ray powder diffraction pattern comprising diffraction peaks at 2-theta values, when measured using Cu K$_\alpha$ radiation, of about 6.29±0.2, 7.90±0.2, 11.89±0.2, 14.78±0.2, 15.16±0.2, 18.27±0.2, 18.77±0.2, 19.43±0.2, 24.34±0.2 and 26.02±0.2.

In one embodiment, the pseudopolymorph of Compound A is a crystalline methanol solvate, having an X-ray powder diffraction pattern with the diffraction peaks listed in the table shown in Example 2.

In another embodiment, the pseudopolymorph of Compound A is a crystalline ethanol solvate, having an X-ray powder diffraction pattern with the diffraction peaks listed in the table shown in Example 3.

In still another embodiment, the pseudopolymorph of Compound A is a crystalline 1-propanol solvate, having an X-ray powder diffraction pattern with the diffraction peaks listed in the table shown in Example 4.

In another embodiment, the pseudopolymorph of Compound A is a crystalline 2-propanol solvate, having an X-ray powder diffraction pattern with the diffraction peaks listed in the table shown in Example 5.

In another embodiment, the pseudopolymorph of Compound A is a crystalline acetone solvate, having an X-ray powder diffraction pattern with the diffraction peaks listed in the table shown in Example 6.

In yet another embodiment, the pseudopolymorph of Compound A is a crystalline 1-butanol solvate, having an X-ray powder diffraction pattern with the diffraction peaks listed in the table shown in Example 7.

In another embodiment, the pseudopolymorph of Compound A is a crystalline ethylene glycol solvate, having an X-ray powder diffraction pattern with the diffraction peaks listed in the table shown in Example 8.

In a further embodiment, the pseudopolymorph of Compound A is a crystalline propylene glycol solvate, having an X-ray powder diffraction pattern with the diffraction peaks listed in the table shown in Example 9.

In another embodiment, the pseudopolymorph of Compound A is a crystalline methyl isobutyl ketone/propylene glycol mixed solvate, having an X-ray powder diffraction pattern with the diffraction peaks listed in the table shown in Example 10.

In another embodiment, the pseudopolymorph of Compound A is a crystalline hydrate, having an X-ray powder diffraction pattern with the diffraction peaks listed in the table shown in Example 11.

In another embodiment, the pseudopolymorph of Compound A is the crystalline methanol solvate of the 1,5-napthalene disulfonic acid salt of Compound A, having an X-ray powder diffraction pattern with the diffraction peaks listed in the table shown in Example 12.

In one aspect, the present invention relates to processes for preparing pseudopolymorphs. Pseudopolymorphs of Compound A are prepared by combining Compound A with an organic solvent, or water, or mixtures of water and water miscible organic solvents, applying any suitable technique to induce crystallization, and isolating the desired pseudopolymorphs. The Pseudopolymorphs of Compound A may be prepared from Compound A using methods known to one skilled in the art of organic synthesis. Methods useful for making the Pseudopolymorphs of Compound A are set forth herein and in the Examples below. Alternative synthetic pathways and analogous structures will be apparent to those skilled in the art of organic synthesis.

Techniques for inducing crystallization are to be understood those processes for the production of crystals, which include but are not limited to, dissolving or dispersing Compound A in a solvent medium, bringing the solution or dispersion of Compound A and the solvent(s) to a desired concentration, bringing the said solution or dispersion to a desired temperature, effecting any suitable pressure, removing and/or separating any undesired material or impurities and optionally drying the formed crystals to obtain the pseudopolymorphs in a solid state, if such a state is desired.

Bringing the solution or dispersion of Compound A and solvents to a desired concentration does not necessarily imply an increase in the concentration of Compound A. In certain cases, a decrease or no change in concentration could be preferable. By bringing the said solution or dispersion to a desired temperature, one will understand the acts of heating, cooling or leaving at room temperature.

The techniques used for obtaining a desired concentration include, but are not limited to, evaporation by atmospheric distillation, vacuum distillation, fractioned distillation, azeotropic distillation, film evaporation, other techniques well known in the art and combinations thereof. An optional process for obtaining a desired concentration could as well involve the saturation of the solution of Compound A and solvent, for example, by adding a sufficient volume of a non-solvent to the solution to reach the saturation point. Other suitable techniques for saturating the solution include the introduction of additional Compound A to the solution and/or evaporation of a portion of the solvent from the solution.

Removing and/or separating any undesired material or impurities may be performed by purification, filtering, washing, precipitation or similar techniques. Separation, for example, can be conducted using known solid-liquid separation techniques. Filtering procedures known to those skilled in the art can also be used in the present process. The filtrations can be performed, amongst other methods, by centrifugation, or using Buchner style filter, Rosenmund filter or plates, or frame press. In one embodiment, in-line filtration or safety filtration may be advantageously used in the processes disclosed above, in order to increase the purity of the resulting pseudopolymorphic form. Additionally, filtering agents such as silica gel, Arbocel®, dicalite diatomite, or the like, may also be used to purify the crystals of interest.

Crystals obtained may be also dried, and such drying process may optionally be used in the different crystallization processes, if more than one crystallization process is applied. Drying procedures useful in the present methods include, but are not limited to, such as heating, applying vacuum, circulating air or gas, adding a desiccant, freeze-drying, spray-drying, evaporating, or the like, or any combination thereof.

Processes for crystallization of pseudopolymorphs of Compound A also include multiple combinations of techniques and variations thereof. As such, and by way of example, crystallization of pseudopolymorphs of Compound A may be executed by dissolving or dispersing Compound A at a suitable temperature in the solvent whereby portion of the said solvent evaporates increasing the concentration of the Compound A in the said solution or dispersion, cooling the said mixture, and optionally washing and/or filtering and drying resulting solvate crystals of Compound A. Optionally, pseudopolymorphs of Compound A may be prepared by dissolving or dispersing Compound A in a solvent medium, cooling said solution or dispersion and subsequently filtering and drying the obtained pseudopolymorph. Another example of preparation of solvates of Compound A could be by saturating Compound A in the solvent medium, and optionally filtering, washing and drying obtained crystals.

Crystal formation may as well involve more than one crystallization process. In certain cases, one, two or more extra crystallization steps may be advantageously performed for different reasons, such as to increase the quality of the resulting solvate. For instance, pseudopolymorphs of the present invention could also be prepared by adding a solvent to an initial starting base material of Compound A, stirring the solution at a fixed temperature until the compound is fully dissolved, concentrating the solution by vacuum distillation, then cooling. A first crystallization would take place and the formed crystals would be washed with a solvent, followed by dissolution of Compound A with the solvent to form the desired pseudopolymorph. Recrystallization of the reaction mixture would occur, followed by a cooling step from elevated temperature. The formed pseudopolymorph would optionally be filtered and dried.

By dissolving or dispersing Compound A in an organic solvent, water or a mixture of water and water miscible organic solvents, one may obtain different degrees of dispersion, such as suspensions, emulsions, slurries, mixtures or homogeneous one-phase solutions.

In one embodiment, the solvent medium may contain additives, for example one or more dispersing agents, surfactants or other additives, or mixtures thereof of the type normally used in the preparation of crystalline suspensions and which are well documented in the literature. The additives may be advantageously used in modifying the shape of crystal by increasing the leniency and decreasing the surface area.

The solvent medium containing the solution may optionally be stirred for a certain period of time, or vigorously agitated using, for example, a high shear mixer or homogeniser or a combination of these, to generate the desired droplet size for the organic compound.

Examples of organic solvents useful for the present invention include, but are not limited to, $C_1$-$C_4$ alcohols such as methanol, ethanol, isopropanol, butanol, 1-methoxy-2-propanol, and the like; $C_2$-$C_4$ glycols such as ethylene glycol, propylene glycol and the like; $C_1$-$C_4$ chloroalkanes such as dichloromethane; $C_1$-$C_4$ ketones such as acetone; $C_1$-$C_4$ ethers such as anisole, and the like; cycloethers such as tetrahydrofuran; $C_1$-$C_4$ esters such as ethylacetate; $C_1$-$C_4$ sulfonates such as mesylate, ethanesulfonate, butanesulfonate, 2-methyl-1-propanesulfonate; and the like.

Examples of mixtures of water and water miscible organic solvents include, but are not limited to, mixtures of water with all organic solvents listed above provided they are miscible in water, e.g., ethanol/water, for instance in a 50/50 ratio.

Preferred solvents are pharmaceutically acceptable solvents. However, pharmaceutically non-acceptable solvents may also find their use in the preparation of pharmaceutically acceptable pseudopolymorphs.

In one embodiment, the solvent is a pharmaceutically acceptable solvent since it results in a pharmaceutically acceptable pseudopolymorph. In a more preferred method, the solvent is ethanol.

In another embodiment, pharmaceutically acceptable pseudopolymorphs of Compound A can be prepared starting from pseudopolymorphic forms of Compound A, which may not be necessarily pharmaceutically acceptable. Pseudopolymorphs may also be prepared from the amorphous form of Compound A.

In the mixtures of water and water miscible organic solvents, the amount of water can vary from about 5% by volume to about 95% by volume, preferably from about 25% to about 75% by volume, more preferably from about 40% to about 60% by volume.

It should also be noted that the quality of selected organic solvent (absolute, denaturated, or other) also influences the resulting quality of the pseudopolymorph.

Control of precipitation temperature and seeding may be additionally used to improve the reproducibility of the crystallization process, the particle size distribution and form of the product. As such, the crystallization can be effected without seeding with crystals of the compound to be crystallized or preferably in the presence of crystals of the compound to be crystallized, which are introduced into the solution by seeding. Seeding can also be effected several times at various temperatures. The amount of the seed material depends on the amount of the solution and can readily be determined by a person skilled in the art.

The time for crystallization in each crystallization step will depend on the conditions applied, the techniques employed and/or solvents used.

Breaking up the large particles or aggregates of particles after crystal conversion may additionally be performed in order to obtain a desired and homogeneous particle size. Accordingly, the solvate crystal forms of Compound A can be optionally milled after undergoing conversion. Milling or grinding refers to physically breaking up the large particles or aggregates of particles using methods and apparatus well known in the art for particle size reduction of powders. Resulting particle sizes may range from millimeters to nanometers, yielding i.e. nanocrystals, micro crystals.

The yield of the preparation process of the pseudopolymorphs of Compound A may be 10% or more. In one embodiment, the yield is from about 40% to about 100%. In one embodiment, the yield is from about 75% to about 100%.

In one embodiment, the pseudopolymorphs of the present invention have a purity greater than 90 percent. In another embodiment, the pseudopolymorphs of the present invention have a purity greater than 95 percent. In still another embodiment, the pseudopolymorphs of the present invention have a purity greater than 99 percent.

In one embodiment, the Pseudopolymorphs of Compound A are in substantially purified form.

Other embodiments of the present invention include the following:

(a) A pharmaceutical composition comprising an effective amount of amorphous Compound A or a pharmaceutically acceptable salt thereof, and a pharmaceutically acceptable carrier.

(b) The pharmaceutical composition of (a), further comprising a second therapeutic agent selected from the group consisting of HCV antiviral agents, immunomodulators, and anti-infective agents.

(c) The pharmaceutical composition of (b), wherein the HCV antiviral agent is an antiviral selected from the group consisting of HCV protease inhibitors and HCV NS5B polymerase inhibitors.

(d) A pharmaceutical combination that is (i) a amorphous Compound A and (ii) a second therapeutic agent selected from the group consisting of HCV antiviral agents, immunomodulators, and anti-infective agents; wherein the amorphous Compound A and the second therapeutic agent are each employed in an amount that renders the combination effective for inhibiting HCV replication, or for treating HCV infection and/or reducing the likelihood or severity of symptoms of HCV infection.

(e) The combination of (d), wherein the HCV antiviral agent is an antiviral selected from the group consisting of HCV protease inhibitors and HCV NS5B polymerase inhibitors.

(f) A method of inhibiting HCV replication in a subject in need thereof which comprises administering to the subject an effective amount of amorphous Compound A.

(g) A method of treating HCV infection and/or reducing the likelihood or severity of symptoms of HCV infection in a subject in need thereof which comprises administering to the subject an effective amount of amorphous Compound A.

(h) The method of (g), wherein the amorphous Compound A is administered in combination with an effective amount of at least one second therapeutic agent selected from the group consisting of HCV antiviral agents, immunomodulators, and anti-infective agents.

(i) The method of (h), wherein the HCV antiviral agent is an antiviral selected from the group consisting of HCV protease inhibitors and HCV NS5B polymerase inhibitors.

(j) A method of inhibiting HCV replication in a subject in need thereof which comprises administering to the subject the pharmaceutical composition of (a), (b) or (c) or the combination of (d) or (e).

(k) A method of treating HCV infection and/or reducing the likelihood or severity of symptoms of HCV infection in a subject in need thereof which comprises administering to the subject the pharmaceutical composition of (a), (b) or (c) or the combination of (d) or (e).

The present invention also includes amorphous Compound A, prepared from the Pseudopolymoprhs of Compound A, for use (i) in, (ii) as a medicament for, or (iii) in the preparation of a medicament for: (a) medicine; (b) inhibiting HCV replication or (c) treating HCV infection and/or reducing the likelihood or severity of symptoms of HCV infection. In these uses, the amorphous Compound A can optionally be employed in combination with one or more second therapeutic agents selected from HCV antiviral agents, anti-infective agents, and immunomodulators.

Additional embodiments of the invention include the pharmaceutical compositions, combinations and methods set forth in (a)-(k) above and the uses set forth in the preceding paragraph, wherein the amorphous Compound A employed therein is a compound made from of a Pseudopolymoprhs of Compound A according to features of the invention described herein. In all of these embodiments, the amorphous Compound A may optionally be used in the form of a pharmaceutically acceptable salt or hydrate as appropriate. It is further to be understood that the embodiments of compositions and methods provided as (a) through (k) above are understood to include all embodiments of the compounds, including such embodiments as result from combinations of embodiments.

Non-limiting examples of the Pseudopolymorphs of Compound A and of solid dispersions comprising amorphous Compound A, and pharmaceutically acceptable salts thereof, include compounds and solid dispersions described herein.

Uses of the Pseudopolymorphs of Compound A

Preparation of Solid Dispersions Comprising Compound A

The psedopolymorphs of Compound A are useful for making solid dispersions comprising compound A. Toward this end, the present invention provides compositions comprising Compound A that are prepared by processes that are suitable for causing a compound (the drug) to form a solid molecular dispersion (also referred to as an amorphous dispersion) in the polymer such that the drug is generally amorphous or dissolved in the polymer(s) and/or other components of the formulation, such as surfactant(s). The dispersions are stable, and the drug does not typically form crystals or other insoluble particles. Methods to produce such dispersions include solution methods, such as spray drying, spray coating, freeze-drying, and evaporation of a co-solvent under vacuum or by heating a solution of polymer and drug. Such methods also include methods that mechanically stress or blend the solid drug with the polymer in the molten or dry state, such as hot melt extrusion, high energy mechanical activation, and methods of compounding the solid non-molten polymer and drug under heat and pressure to form a dispersion.

In one aspect, the present invention provides a method of making a pharmaceutical composition comprising an amorphous form of Compound A, wherein said method comprises the steps: (a) rendering a pseudopolymorph of Compound A amorphous; and (b) putting a pharmaceutically effective amount of the amorphous form of Compound A into a dosage form.

In another aspect, the present invention provides a method of making a pharmaceutical composition comprising the steps: (a) rendering a pseudopolymorph of Compound A amorphous, wherein the pseudopolymorph of Compound A is selected from Form A (methanolate), Form B (ethanolate), Form C (1-propanolate), Form D (2-propanolate), Form E (acetonate), Form F (1-butanolate), Form G (ethylene glycolate), Form H (propylene glycolate), Form I (methyl isobutyl ketone/propylene glycol mixed solvate), Form J (hydrate) and Form K (1,5-naphthalene disulfonic acid salt methanol solvate); and (b) putting a pharmaceutically effective amount of the amorphous form of Compound A into a dosage form.

In one embodiment, in step (a), the pseudopolymorph of Compound A is rendered amorphous using a method selected from spray drying, spray coating, freeze-drying, evaporation of a co-solvent under vacuum or by heating a solution of polymer and drug, methods that blend a solid drug with a polymer in the molten state, such as hot melt extrusion, and methods of compounding the solid non-molten polymer and drug under heat and pressure to form a dispersion.

In one embodiment, in step (a), the pseudopolymorph of Compound A is rendered amorphous using spray drying.

In another embodiment, in step (a), the pseudopolymorph of Compound A is rendered amorphous using hot melt extrusion.

In another aspect, the present invention provides pharmaceutical compositions comprising:

(1) Compound A, or a pharmaceutically acceptable salt thereof;

(2) a concentration-enhancing polymer, where the polymer increases the bioavailability or enhances the dissolution behavior of Compound A, and is water soluble or readily disperses in water; and (3) optionally one or more surfactants.

A "concentration-enhancing polymer" is a polymer that can form an amorphous dispersion with Compound A, by (a) dissolving the Compound A or (b) interacting with the Compound A in such a way that the Compound A does not form crystals or crystalline domains in the polymer. A concentration-enhancing polymer is water soluble or readily dispersed in water, so that when the polymer is placed in water or an aqueous environment (e.g. fluids in the gastrointestinal (GI) tract or simulated GI fluids), the solubility and/or bioavailability of Compound A is increased over the solubility or bioavailability in the absence of the polymer.

An embodiment of the present invention is directed to a pharmaceutical composition that comprises a concentration-enhancing polymer and 4-40% of Compound A, or a pharmaceutically acceptable salt thereof. An embodiment of the present invention is directed to a pharmaceutical composition that comprises a concentration-enhancing polymer and 6-20% of Compound A, or a pharmaceutically acceptable salt thereof. An embodiment of the present invention is directed to a pharmaceutical composition that comprises a concentration-enhancing polymer and 8-15% of Compound A, or a pharmaceutically acceptable salt thereof. In an embodiment of the present invention, formulations of copovidone with Compound A and an optional surfactant may comprise 4%-40% Compound A and 0-10% surfactant.

Another aspect of the present invention is directed to a process for preparing a composition comprising Compound A, or a pharmaceutically acceptable salt thereof molecularly dispersed in or dissolved in a concentration-enhancing polymer. In some embodiments it is preferred to select the polymer used in a composition of the invention from those concentration-enhancing polymers providing the following properties: (i) Compound A is soluble in the polymer; (ii) Compound A forms a solution or dispersion behaving as a eutectic which has a melting point below the melting point of Compound A; (iii) when Compound A is admixed with the selected polymer(s) and heated it apparently acts as a fluxing agent to promote melting the polymer and promote dissolution of Compound A into the polymer. In some embodiments the process for preparing a composition of the invention comprises: (i) forming a admixture of Compound A and the selected polymer; (ii) forming a molten dispersion by heating the admixture to a temperature above about 60° C. and below about 200° C., optionally with stirring of the molten dispersion; (iii) cooling the dispersion provided in Step (ii) to form a solid; and (iv) optionally forming a shaped mass from the dispersion either before or contemporaneously with Cooling Step (iii).

Processes for making pharmaceutical compositions of Compound A with a concentration-enhancing polymer include (a) hot melt extrusion and (b) spray drying Both of these processes are well known in the art. In spray drying, the polymer, active compound, and other optional ingredients, such as surfactants, are dissolved in a solvent and are then sprayed through a nozzle as a fine spray into a chamber where the solvent is evaporated quickly to make fine particles comprising polymer, drug, and optional other ingredients. The solvent is any solvent in which all of the components of the composition are soluble and which is readily evaporated in a spray drier. The solvent should also be suitable for use in preparing pharmaceutical compositions. In hot melt extrusion, the polymer, drug, and optional surfactants are mixed together in a wet granulation process or other mixing process, and then the mixture of polymer, drug and surfactant are fed into the chamber of an extruder, preferably a twin screw extruder to obtain better mixing, and are then thoroughly melted and mixed to make an amorphous dispersion.

In accordance with the present invention, a melt can be prepared in any convenient apparatus in which an admixture of Compound A and polymer can be heated and optionally stirred. Solidification can be carried out by merely cooling the melt by any means convenient and in any container convenient. Once a solid is obtained, the solid can be further mechanically processed to provide a convenient form for incorporation into a medicament, for example, tablets or capsules.

It will be appreciated that other methods of preparing a melt, solidifying it, and forming the solid into conveniently sized particles can be utilized without departing from the scope of the invention. For example, conveniently, compositions of the invention may be prepared using an extruder. When an extruder is employed to prepare compositions of the invention, conveniently, the material may be introduced into the extruder either in a pre-flux state, that is, as a dry admixture, or in a fluxed state, that is in a melted, plastic, or semi-solid state achieved after the application of sufficient heat to the admixture to cause the Compound A to dissolve in the polymer, optionally when a fluxed charge is prepared, blending may be employed during heating to promote uniformity of the fluxed material.

If the material is introduced to the extruder in a fluxed state, residence time in the extruder is selected to be just sufficient to insure homogeneity of the composition and the temperature is preferably maintained in the extruder at a level just sufficient to insure that the material maintains its plasticity so that it can be extruded into a conveniently shaped extrudate. If the material is introduced into an extruder in a pre-flux state, the extruder components, for example, the barrels and any mixing chamber present in the equipment, will be maintained at a temperature sufficient to promote fluxing of the admixture. Temperatures selected for use in processing a composition will also take into account that blending which occurs within the extruder equipment, for example, in a mixing section of the barrels, will also contribute to localized fluxing of the admixture by imparting shear-stresses that induce heating in the mixture. Additionally it will be appreciated that equipment temperatures and residence times will be selected to minimize the amount of time that the admixture placed into the extruder spends under conditions of heating and/or shear stress so as to minimize the amount of Compound A which is decomposed during formation of the composition, as discussed above. In general, extrusion processes in which heating is applied to the material extruded are termed "hot-melt/extrusion processes." When compositions of the present invention are prepared using extruder equipment, the extrudate thus provided can be in any convenient shape, for example, noodles, cylinders, bars, or the like. If desired, the extrudate can be further processed, for example by milling, to provide a particulate form of the composition.

In an alternate embodiment, the present invention is directed to an amorphous form of the compound Compound A. In an alternate embodiment, the present invention is directed to an isolated amorphous form of the compound Compound A. In an embodiment of the present invention, the pharmaceutical composition of Compound A and concentration-enhancing polymer is prepared according to any known process which results in at least a major portion of Compound A is present in the amorphous state relative to other morphological forms of Compound A. These processes include mechanical processes, such as milling and extrusion; melt processes, such as high temperature fusion, hot melt extrusion, solvent modified fusion, and melt congealing processes; and solvent processes, including non-solvent precipitation processes, spray coating, and spray-drying. Although the dispersions of the present invention may be made by any of these processes, in an embodiment of the invention Compound A in the pharmaceutical composition is substantially amorphous and is substantially homogeneously distributed throughout the polymer.

In an alternate embodiment, the present invention is directed to Compound A in a form which contains at least about 40 wt. % of the amorphous form relative to other morphological forms of Compound A. In an alternate embodiment, the present invention is directed to Compound A in a form which contains at least about 50 wt. % of the amorphous form relative to other morphological forms of Compound A. In an alternate embodiment, the present invention is directed to Compound A in a form which contains at least about 60 wt. % of the amorphous form relative to other morphological forms of Compound A. In an alternate embodiment, the present invention is directed to Compound A in a form which contains at least about 70 wt. % of the amorphous form relative to other morphological forms of Compound A. In an alternate embodiment, the present invention is directed to Compound A in a form which contains at least about 80 wt. % of the amorphous form relative to other morphological forms of Compound A. In an alternate embodiment, the present invention is directed to Compound A in a form which contains at least about 90 wt. % of the amorphous form relative to other morphological forms of Compound A. In an alternate embodiment, the present invention is directed to Compound A in a form which contains at least about 95 wt. % of the amorphous form relative to other morphological forms of Compound A. In an alternate embodiment, the present invention is directed to Compound A in a form which contains at least about 98 wt. % of the amorphous form relative to other morphological forms of Compound A. In an alternate embodiment, the present invention is directed to Compound A in a form which contains at least about 99 wt. % of the amorphous form relative to other morphological forms of Compound A. The relative amounts of crystalline and amorphous Compound A can be determined by several analytical methods, including differential scanning calorimetry (DSC), x-ray powder diffraction (XRPD) and Raman spectroscopy.

The amorphous form of the compound Compound A may have benefits relative to other morphological forms of Compound A such as greater solubility and/or a faster dissolution rate than crystalline forms of the compound, which may improve bioavailability of the compound, may facilitate a faster onset of therapeutic action, may reduce variability of therapeutic response among subjects, and may reduce any food effect. In one embodiment, the pharmaceutical composition comprising Compound A is a solid molecular dispersion.

In one embodiment, the pharmaceutical composition comprising Compound A is a solid molecular dispersion comprising Compound A in amorphous form.

In another embodiment, the solid molecular dispersion comprising Compound A is milled or granulated to provide a particulate product.

In one embodiment, the present invention provides methods for treating a patient infected with HCV comprising administering to the patient a solid molecular dispersion formulation comprising Compound A.

Uses of Compound A

Treatment or Prevention of a Flaviviridae Virus

Compound A can be useful for treating or preventing a viral infection caused by the Flaviviridae family of viruses. In one embodiment, the Flaviviridae infection being treated is hepatitis C virus infection.

Treatment or Prevention of HCV Infection

Compound A is useful in the inhibition of HCV (e.g., HCV NS5A), the treatment of HCV infection and/or reduction of the likelihood or severity of symptoms of HCV infection and the inhibition of HCV viral replication and/or HCV viral production in a cell-based system. For example, Compound A is useful in treating infection by HCV after suspected past exposure to HCV by such means as blood transfusion, exchange of body fluids, bites, accidental needle stick, or exposure to patient blood during surgery or other medical procedures.

In one embodiment, the hepatitis C infection is acute hepatitis C. In another embodiment, the hepatitis C infection is chronic hepatitis C.

Accordingly, in one embodiment, the invention provides methods for treating HCV infection in a patient, the methods comprising administering to the patient an effective amount of Compound A or a pharmaceutically acceptable salt thereof. In a specific embodiment, the amount administered is effective to treat or prevent infection by HCV in the patient. In another specific embodiment, the amount administered is effective to inhibit HCV viral replication and/or viral production in the patient.

The Pseudopolymorphs of Compound A are also useful in the preparation and execution of screening assays for antiviral compounds. For example Compound A is useful for identifying resistant HCV replicon cell lines harboring mutations within NS5A, which are excellent screening tools for more powerful antiviral compounds. Furthermore, Compound A is useful in establishing or determining the binding site of other antivirals to the HCV replicase.

Compositions and Administration

When administered to a patient, Compound A can be administered as a component of a composition that comprises a pharmaceutically acceptable carrier or vehicle. The present invention provides pharmaceutical compositions comprising an effective amount of Compound A and a pharmaceutically acceptable carrier. In the pharmaceutical compositions and methods of the present invention, the active ingredients will typically be administered in admixture with suitable carrier materials suitably selected with respect to the intended form of administration, i.e., oral tablets, capsules (either solid-filled, semi-solid filled or liquid filled), powders for constitution, oral gels, elixirs, dispersible granules, syrups, suspensions, and the like, and consistent with conventional pharmaceutical practices. For example, for oral administration in the form of tablets or capsules, the active drug component may be combined with any oral non-toxic pharmaceutically acceptable inert carrier, such as lactose, starch, sucrose, cellulose, magnesium stearate, dicalcium phosphate, calcium sulfate, talc, mannitol, ethyl alcohol (liquid forms) and the like. Solid form preparations include powders, tablets, dispersible granules, capsules, cachets and suppositories. Powders and tablets may be comprised of from about 0.5 to about 95 percent inventive composition. Tablets, powders, cachets and capsules can be used as solid dosage forms suitable for oral administration.

Moreover, when desired or needed, suitable binders, lubricants, disintegrating agents and coloring agents may also be incorporated in the mixture. Suitable binders include starch, gelatin, natural sugars, corn sweeteners, natural and synthetic gums such as acacia, sodium alginate, carboxymethylcellulose, polyethylene glycol and waxes. Among the lubricants there may be mentioned for use in these dosage forms, boric acid, sodium benzoate, sodium acetate, sodium chloride, and the like. Disintegrants include starch, methylcellulose, guar gum, and the like. Sweetening and flavoring agents and preservatives may also be included where appropriate.

Also included are solid form preparations which are intended to be converted, shortly before use, to liquid form preparations for either oral or parenteral administration. Such liquid forms include solutions, suspensions and emulsions.

For preparing suppositories, a low melting wax such as a mixture of fatty acid glycerides or cocoa butter is first melted, and the active ingredient is dispersed homogeneously therein as by stirring. The molten homogeneous mixture is then poured into convenient sized molds, allowed to cool and thereby solidify.

Additionally, the compositions of the present invention may be formulated in sustained release form to provide the rate controlled release of any one or more of the components or active ingredients to optimize therapeutic effects, i.e., antiviral activity and the like. Suitable dosage forms for sustained release include layered tablets containing layers of varying disintegration rates or controlled release polymeric matrices impregnated with the active components and shaped in tablet form or capsules containing such impregnated or encapsulated porous polymeric matrices.

In one embodiment, Compound A is administered orally.

In another embodiment, Compound A is administered intravenously.

In another embodiment, Compound A is administered topically.

In still another embodiment, Compound A is administered sublingually.

In one embodiment, a pharmaceutical preparation comprising Compound A is in unit dosage form. In such form, the preparation is subdivided into unit doses containing effective amounts of the active components.

Compositions can be prepared using techniques such as conventional mixing, granulating or coating methods; and by using solid dispersion based upon the guidance provided herein. In one embodiment, the present compositions can contain from about 0.1% to about 99% of Compound A by weight or volume. In various embodiments, the present compositions can contain, in one embodiment, from about 1% to about 70% or from about 5% to about 60% of Compound A by weight or volume.

The quantity of Compound A in a unit dose of preparation may be varied or adjusted from about 1 mg to about 2500 mg. In various embodiments, the quantity is from about 10 mg to about 1000 mg, 1 mg to about 500 mg, 1 mg to about 100 mg, and 1 mg to about 100 mg.

The doses and dosage regimen of the other agents used in the combination therapies of the present invention for the treatment or prevention of HCV infection can be determined by the attending clinician, taking into consideration the approved doses and dosage regimen in the package insert; the age, sex and general health of the patient; and the type and severity of the viral infection or related disease or disorder. When administered in combination, Compound A and the other agent(s) can be administered simultaneously (i.e., in the same composition or in separate compositions one right after the other) or sequentially. This particularly useful when the components of the combination are given on different dosing schedules, e.g., one component is administered once daily and another component is administered every six hours, or when the preferred pharmaceutical compositions are different, e.g., one is a tablet and one is a capsule. A kit comprising the separate dosage forms is therefore advantageous.

Generally, a total daily dosage of Compound A alone, or when administered as combination therapy, can range from about 1 to about 2500 mg per day, although variations will necessarily occur depending on the target of therapy, the patient and the route of administration. In one embodiment, the dosage is from about 10 to about 1000 mg/day, administered in a single dose or in 2-4 divided doses. In another embodiment, the dosage is from about 1 to about 500 mg/day, administered in a single dose or in 2-4 divided doses. In still another embodiment, the dosage is from about 1 to about 100 mg/day, administered in a single dose or in 2-4 divided doses. In yet another embodiment, the dosage is from about 1 to about 50 mg/day, administered in a single dose or in 2-4 divided doses. In another embodiment, the dosage is from about 500 to about 1500 mg/day, administered in a single dose or in 2-4 divided doses. In still another embodiment, the dosage is from about 500 to about 1000 mg/day, administered in a single dose or in 2-4 divided doses. In yet another embodiment, the dosage is from about 100 to about 500 mg/day, administered in a single dose or in 2-4 divided doses.

For convenience, the total daily dosage may be divided and administered in portions during the day if desired. In one embodiment, the daily dosage is administered in one portion. In another embodiment, the total daily dosage is administered in two divided doses over a 24 hour period. In another embodiment, the total daily dosage is administered in three divided doses over a 24 hour period. In still another embodiment, the total daily dosage is administered in four divided doses over a 24 hour period.

The amount and frequency of administration of Compound A will be regulated according to the judgment of the attending clinician considering such factors as age, condition and size of the patient as well as severity of the symptoms being treated. Generally, a total daily dosage of Compound A range from about 0.1 to about 2000 mg per day, although variations will necessarily occur depending on the target of therapy, the patient and the route of administration. In one embodiment, the dosage is from about 1 to about 200 mg/day, administered in a single dose or in 2-4 divided doses. In another embodiment, the dosage is from about 10 to about 2000 mg/day, administered in a single dose or in 2-4 divided doses. In another embodiment, the dosage is from about 100 to about 2000 mg/day, administered in a single dose or in 2-4 divided doses. In still another embodiment, the dosage is from about 500 to about 2000 mg/day, administered in a single dose or in 2-4 divided doses.

The compositions of the invention can further comprise one or more additional therapeutic agents, selected from those listed above herein. Accordingly, in one embodiment, the present invention provides compositions comprising: (i) Compound A or a pharmaceutically acceptable salt thereof; (ii) one or more additional therapeutic agents that are not Compound A; and (iii) a pharmaceutically acceptable carrier, wherein the amounts in the composition are together effective to treat HCV infection.

In one embodiment, the present invention provides compositions comprising Compound A and a pharmaceutically acceptable carrier.

In another embodiment, the present invention provides compositions comprising Compound A, a pharmaceutically acceptable carrier, and a second therapeutic agent selected from the group consisting of HCV antiviral agents, immunomodulators, and anti-infective agents.

In another embodiment, the present invention provides compositions comprising Compound A, a pharmaceutically acceptable carrier, and two additional therapeutic agents, each of which are independently selected from the group consisting of HCV antiviral agents, immunomodulators, and anti-infective agents.

Combination Therapy

In another embodiment, the present methods for treating or preventing HCV infection can further comprise the administration of one or more additional therapeutic agents that are other than Compound A.

In one embodiment, the additional therapeutic agent is an antiviral agent.

In another embodiment, the additional therapeutic agent is an immunomodulatory agent, such as an immunosuppressive agent.

Accordingly, in one embodiment, the present invention provides methods for treating a viral infection in a patient, the method comprising administering to the patient: (i) Compound A, or a pharmaceutically acceptable salt thereof, and (ii) at least one additional therapeutic agent that is other than Compound A, wherein the amounts administered are together effective to treat or prevent a viral infection.

When administering a combination therapy of the invention to a patient, therapeutic agents in the combination, or a pharmaceutical composition or compositions comprising therapeutic agents, may be administered in any order such as, for example, sequentially, concurrently, together, simultaneously and the like. The amounts of the various actives in such combination therapy may be different amounts (different dosage amounts) or same amounts (same dosage amounts). Thus, for non-limiting illustration purposes, Compound A and an additional therapeutic agent may be present in fixed amounts (dosage amounts) in a single dosage unit (e.g., a capsule, a tablet and the like).

In one embodiment, Compound A is administered during a time when the additional therapeutic agent(s) exert their prophylactic or therapeutic effect, or vice versa.

In another embodiment, Compound A and the additional therapeutic agent(s) are administered in doses commonly employed when such agents are used as monotherapy for treating a viral infection.

In another embodiment, Compound A and the additional therapeutic agent(s) are administered in doses lower than the doses commonly employed when such agents are used as monotherapy for treating a viral infection.

In still another embodiment, Compound A and the additional therapeutic agent(s) act synergistically and are administered in doses lower than the doses commonly employed when such agents are used as monotherapy for treating a viral infection.

In one embodiment, Compound A and the additional therapeutic agent(s) are present in the same composition. In one embodiment, this composition is suitable for oral administration. In another embodiment, this composition is suitable for intravenous administration. In another embodiment, this composition is suitable for subcutaneous administration. In still another embodiment, this composition is suitable for parenteral administration.

Viral infections and virus-related disorders that can be treated or prevented using the combination therapy methods of the present invention include, but are not limited to, those listed above.

In one embodiment, the viral infection is HCV infection.

The Compound A and the additional therapeutic agent(s) can act additively or synergistically. A synergistic combination may allow the use of lower dosages of one or more agents and/or less frequent administration of one or more agents of a combination therapy. A lower dosage or less frequent administration of one or more agents may lower toxicity of therapy without reducing the efficacy of therapy.

In one embodiment, the administration of Compound A and the additional therapeutic agent(s) may inhibit the resistance of a viral infection to these agents.

Non-limiting examples of additional therapeutic agents useful in the present compositions and methods include an interferon, an immunomodulator, a viral replication inhibitor, an antisense agent, a therapeutic vaccine, a viral polymerase inhibitor, a nucleoside inhibitor, a viral protease inhibitor, a viral helicase inhibitor, a virion production inhibitor, a viral entry inhibitor, a viral assembly inhibitor, an antibody therapy (monoclonal or polyclonal), and any agent useful for treating an RNA-dependent polymerase-related disorder.

In one embodiment, the additional therapeutic agent is a viral protease inhibitor.

In another embodiment, the additional therapeutic agent is a viral replication inhibitor.

In another embodiment, the additional therapeutic agent is an HCV NS3 protease inhibitor.

In still another embodiment, the additional therapeutic agent is an HCV NS5B polymerase inhibitor.

In another embodiment, the additional therapeutic agent is a nucleoside inhibitor.

In another embodiment, the additional therapeutic agent is an interferon.

In yet another embodiment, the additional therapeutic agent is an HCV replicase inhibitor.

In another embodiment, the additional therapeutic agent is an antisense agent.

In another embodiment, the additional therapeutic agent is a therapeutic vaccine.

In a further embodiment, the additional therapeutic agent is a virion production inhibitor.

In another embodiment, the additional therapeutic agent is an antibody therapy.

In another embodiment, the additional therapeutic agent is an HCV NS2 inhibitor.

In still another embodiment, the additional therapeutic agent is an HCV NS4A inhibitor.

In another embodiment, the additional therapeutic agent is an HCV NS4B inhibitor.

In another embodiment, the additional therapeutic agent is an HCV NS5A inhibitor In yet another embodiment, the additional therapeutic agent is an HCV NS3 helicase inhibitor.

In another embodiment, the additional therapeutic agent is an HCV IRES inhibitor.

In another embodiment, the additional therapeutic agent is an HCV p7 inhibitor.

In a further embodiment, the additional therapeutic agent is an HCV entry inhibitor.

In another embodiment, the additional therapeutic agent is an HCV assembly inhibitor.

In one embodiment, the additional therapeutic agents comprise a viral protease inhibitor and a viral polymerase inhibitor.

In still another embodiment, the additional therapeutic agents comprise a viral protease inhibitor and an immunomodulatory agent.

In yet another embodiment, the additional therapeutic agents comprise a polymerase inhibitor and an immunomodulatory agent.

In another embodiment, the additional therapeutic agents comprise a viral protease inhibitor and a nucleoside.

In another embodiment, the additional therapeutic agents comprise an immunomodulatory agent and a nucleoside.

In one embodiment, the additional therapeutic agents comprise an HCV protease inhibitor and an HCV polymerase inhibitor.

In another embodiment, the additional therapeutic agents comprise a nucleoside and an HCV NS5A inhibitor.

In another embodiment, the additional therapeutic agents comprise a viral protease inhibitor, an immunomodulatory agent and a nucleoside.

In a further embodiment, the additional therapeutic agents comprise a viral protease inhibitor, a viral polymerase inhibitor and an immunomodulatory agent.

In another embodiment, the additional therapeutic agent is ribavirin.

HCV polymerase inhibitors useful in the present compositions and methods include, but are not limited to, VP-19744 (Wyeth/ViroPharma), PSI-7851 (Pharmasset), R7128 (Roche/Pharmasset), PF-868554/filibuvir (Pfizer), VCH-759 (ViroChem Pharma), HCV-796 (Wyeth/ViroPharma), IDX-184 (Idenix), IDX-375 (Idenix), NM-283 (Idenix/Novartis), R-1626 (Roche), MK-0608 (Isis/Merck), INX-8014 (Inhibitex), INX-8018 (Inhibitex), INX-189 (Inhibitex), GS 9190 (Gilead), A-848837 (Abbott), ABT-333 (Abbott), ABT-072 (Abbott), A-837093 (Abbott), BI-207127 (Boehringer-Ingelheim), BILB-1941 (Boehringer-Ingelheim), MK-3281 (Merck), VCH222 (ViroChem), VCH916 (ViroChem), VCH716 (ViroChem), GSK-71185 (Glaxo SmithKline), ANA598 (Anadys), GSK-625433 (Glaxo SmithKline), XTL-2125 (XTL Biopharmaceuticals), and those disclosed in Ni et al., *Current Opinion in Drug Discovery and Development*, 7(4):446 (2004); Tan et al., *Nature Reviews*, 1:867 (2002); and Beaulieu et al., *Current Opinion in Investigational Drugs*, 5:838 (2004).

Other HCV polymerase inhibitors useful in the present compositions and methods include, but are not limited to, those disclosed in International Publication Nos. WO 08/082484, WO 08/082488, WO 08/083351, WO 08/136815, WO 09/032116, WO 09/032123, WO 09/032124 and WO 09/032125.

Interferons useful in the present compositions and methods include, but are not limited to, interferon alfa-2a, interferon alfa-2b, interferon alfacon-1 and PEG-interferon alpha conjugates. "PEG-interferon alpha conjugates" are interferon alpha molecules covalently attached to a PEG molecule. Illustrative PEG-interferon alpha conjugates include interferon alpha-2a (Roferon™, Hoffman La-Roche, Nutley, N.J.) in the form of pegylated interferon alpha-2a (e.g., as sold under the trade name Pegasys™), interferon alpha-2b (Intron™, from Schering-Plough Corporation) in the form of pegylated interferon alpha-2b (e.g., as sold under the trade name PEG-Intron™ from Schering-Plough Corporation), interferon alpha-2b-XL (e.g., as sold under the trade name PEG-Intron™), interferon alpha-2c (Berofor Alpha™, Boehringer Ingelheim, Ingelheim, Germany), PEG-interferon lambda (Bristol-Myers Squibb and ZymoGenetics), interferon alfa-2b alpha fusion polypeptides, interferon fused with the human blood protein albumin (Albuferon™, Human Genome Sciences), Omega Interferon (Intarcia), Locteron controlled release interferon (Biolex/OctoPlus), Biomed-510 (omega interferon), Peg-IL-29 (ZymoGenetics), Locteron CR (Octoplus), IFN-α-2b-XL (Flamel Technologies), and consensus interferon as defined by determination of a consensus sequence of naturally occurring interferon alphas (Infergen™, Amgen, Thousand Oaks, Calif.).

Antibody therapy agents useful in the present compositions and methods include, but are not limited to, antibodies specific to IL-10 (such as those disclosed in US Patent Publication No. US2005/0101770, humanized 12G8, a humanized monoclonal antibody against human IL-10, plasmids containing the nucleic acids encoding the humanized 12G8 light and heavy chains were deposited with the American Type Culture Collection (ATCC) as deposit numbers PTA-5923 and PTA-5922, respectively), and the like).

Examples of viral protease inhibitors useful in the present compositions and methods include, but are not limited to, an HCV protease inhibitor.

HCV protease inhibitors useful in the present compositions and methods include, but are not limited to, those disclosed in U.S. Pat. Nos. 7,494,988, 7,485,625, 7,449,447, 7,442,695, 7,425,576, 7,342,041, 7,253,160, 7,244,721, 7,205,330, 7,192,957, 7,186,747, 7,173,057, 7,169,760, 7,012,066, 6,914,122, 6,911,428, 6,894,072, 6,846,802, 6,838,475, 6,800,434, 6,767,991, 5,017,380, 4,933,443, 4,812,561 and 4,634,697; U.S. Patent Publication Nos. US20020068702, US20020160962, US20050119168, US20050176648, US20050209164, US20050249702 and US20070042968; and International Publication Nos. WO 03/006490, WO 03/087092, WO 04/092161 and WO 08/124148.

Additional HCV protease inhibitors useful in the present compositions and methods include, but are not limited to, SCHSO3034 (Boceprevir, Schering-Plough), SCH900518 (Schering-Plough), VX-950 (Telaprevir, Vertex), VX-500 (Vertex), VX-813 (Vertex), VBY-376 (Virobay), BI-201335 (Boehringer Ingelheim), TMC-435 (Medivir/Tibotec), ABT-450 (Abbott), TMC-435350 (Medivir), ITMN-191/R7227 (InterMune/Roche), EA-058 (Abbott/Enanta), EA-063 (Abbott/Enanta), GS-9132 (Gilead/Achillion), ACH-1095 (Gilead/Achillon), IDX-136 (Idenix), IDX-316 (Idenix), ITMN-8356 (InterMune), ITMN-8347 (InterMune), ITMN-8096 (InterMune), ITMN-7587 (InterMune), BMS-650032 (Bristol-Myers Squibb), VX-985 (Vertex) and PHX1766 (Phenomix).

Further examples of HCV protease inhibitors useful in the present compositions and methods include, but are not limited to, those disclosed in Landro et al., *Biochemistry*, 36(31):9340-9348 (1997); Ingallinella et al., *Biochemistry*, 37(25):8906-8914 (1998); Llinàs-Brunet et al., *Bioorg Med Chem Lett*, 8(13):1713-1718 (1998); Martin et al., *Biochemistry*, 37(33):11459-11468 (1998); Dimasi et al., *J Virol*, 71(10):7461-7469 (1997); Martin et al., *Protein Eng*, 10(5): 607-614 (1997); Elzouki et al., *J Hepat*, 27(1):42-48 (1997); *BioWorld Today*, 9(217):4 (Nov. 10, 1998); U.S. Patent Publication Nos. US2005/0249702 and US 2007/0274951; and International Publication Nos. WO 98/14181, WO 98/17679, WO 98/17679, WO 98/22496 and WO 99/07734 and WO 05/087731.

Further examples of HCV protease inhibitors useful in the present compositions and methods include, but are not limited to, the following compounds:

27
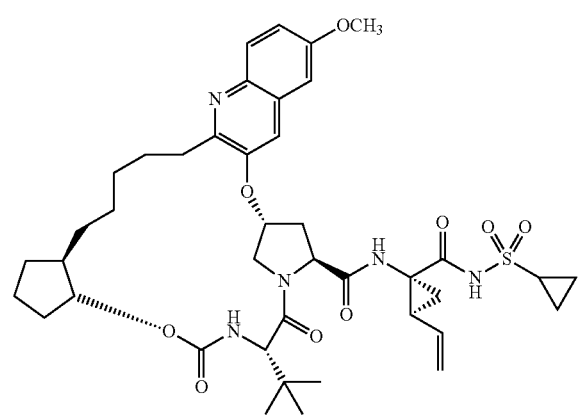
28
-continued
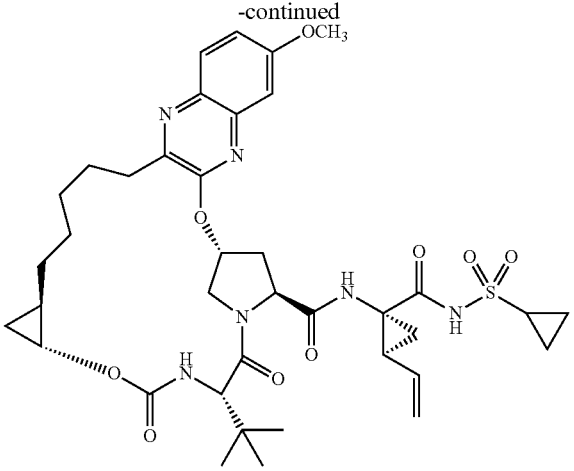
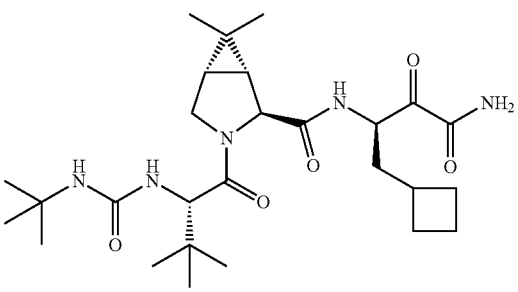
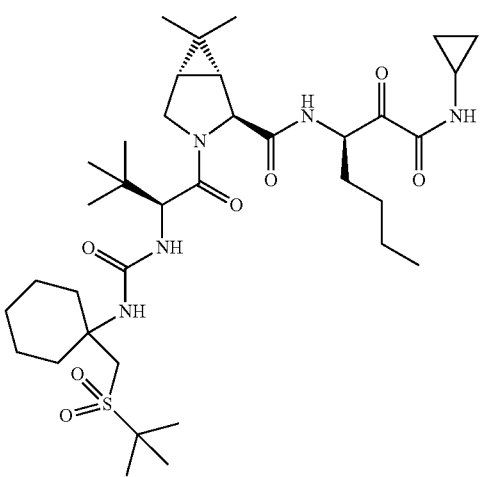

29
-continued
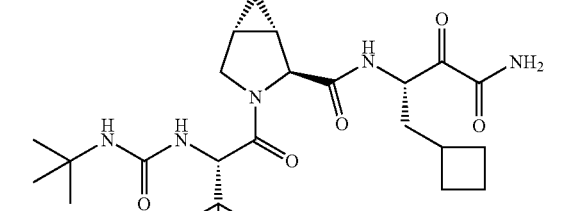
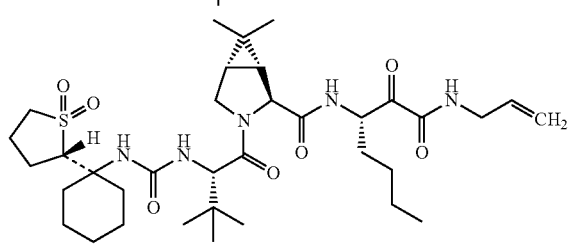
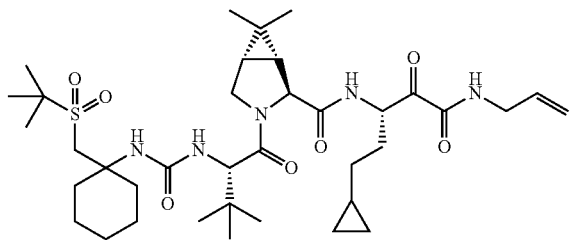
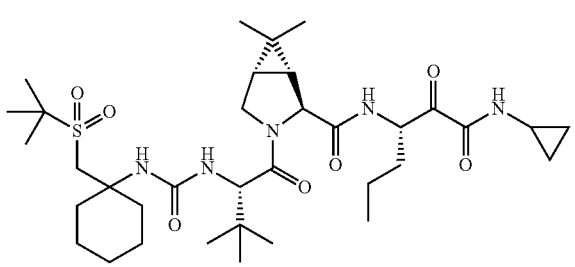
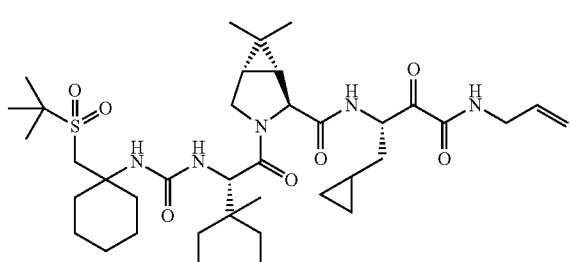
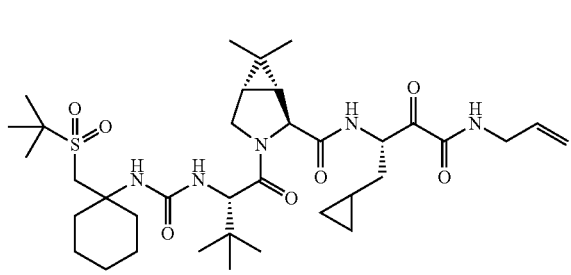
30
-continued
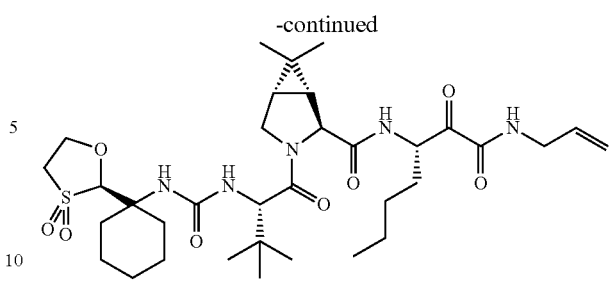
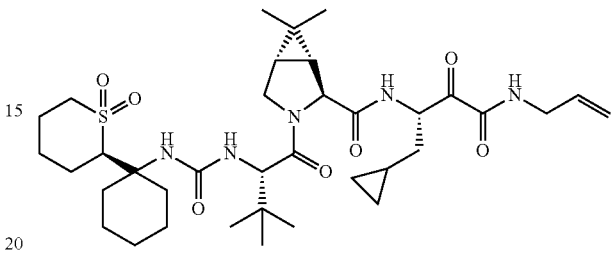
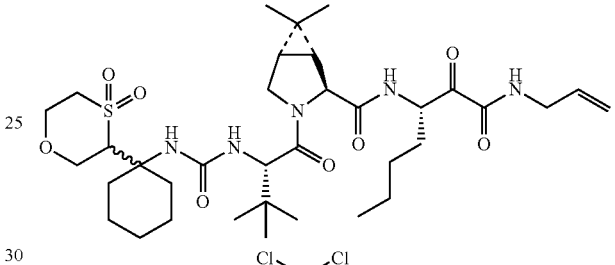
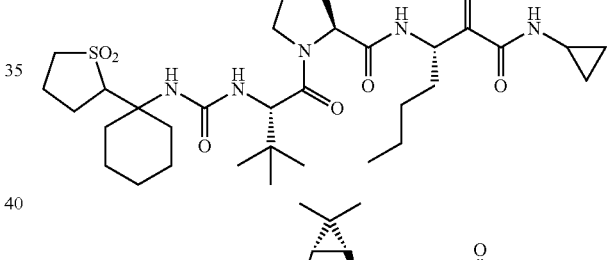
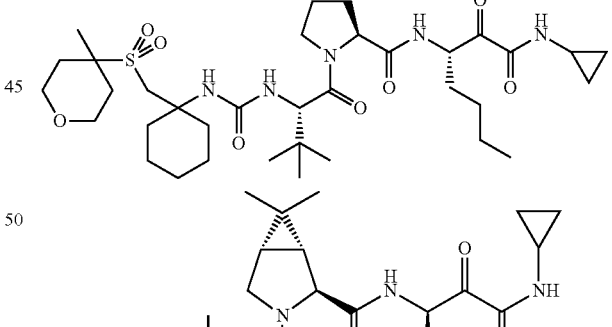
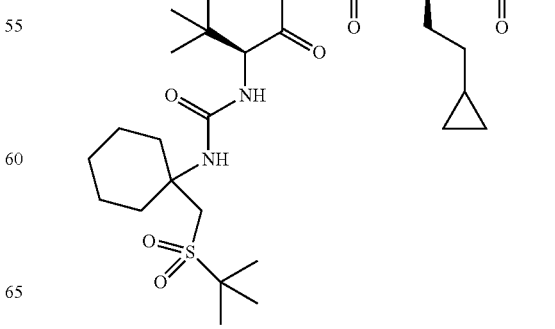

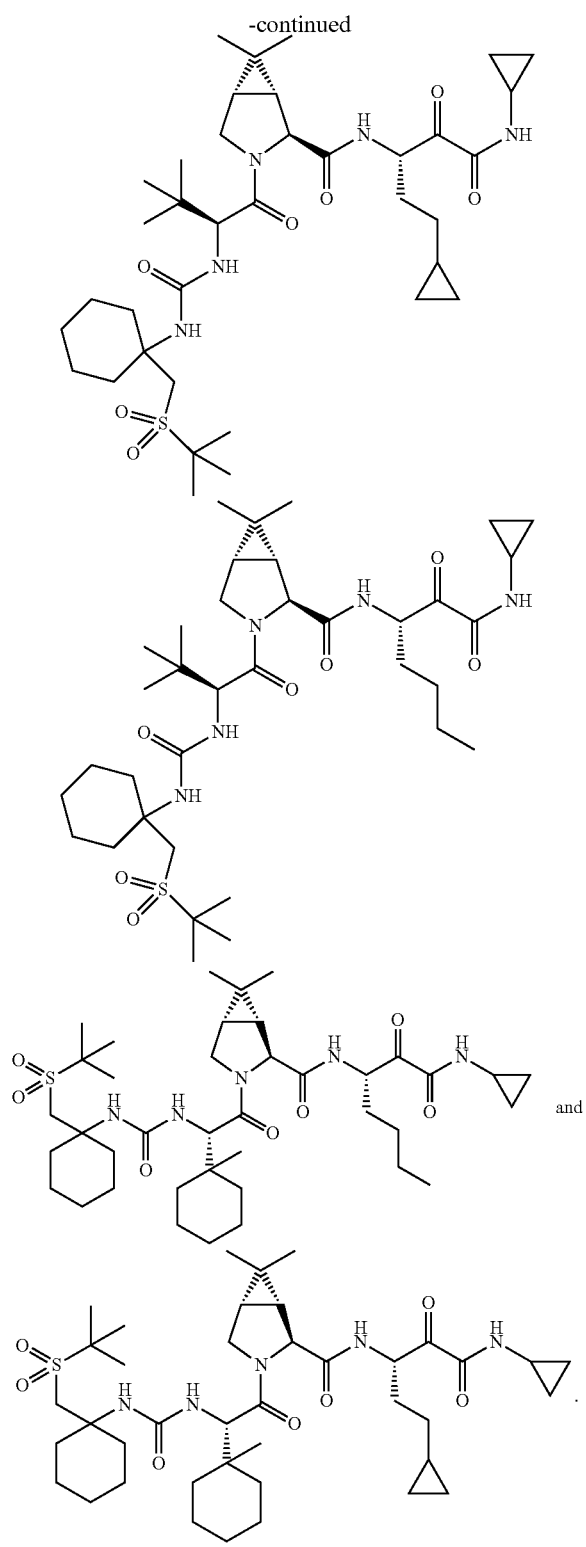

Viral replication inhibitors useful in the present compositions and methods include, but are not limited to, HCV replicase inhibitors, IRES inhibitors, NS4A inhibitors, NS3 helicase inhibitors, NS5A inhibitors, NS5B inhibitors, ribavirin, AZD-2836 (Astra Zeneca), BMS-790052 (Bristol-Myers Squibb, see Gao et al., Nature, 465:96-100 (2010)), viramidine, A-831 (Arrow Therapeutics); an antisense agent or a therapeutic vaccine.

HCV NS4A inhibitors useful in the useful in the present compositions and methods include, but are not limited to, those disclosed in U.S. Pat. Nos. 7,476,686 and 7,273,885; U.S. Patent Publication No. US20090022688; and International Publication Nos. WO 2006/019831 and WO 2006/019832. Additional HCV NS4A inhibitors useful in the useful in the present compositions and methods include, but are not limited to, AZD2836 (Astra Zeneca) and ACH-806 (Achillon Pharmaceuticals, New Haven, Conn.).

HCV replicase inhibitors useful in the useful in the present compositions and methods include, but are not limited to, those disclosed in U.S. Patent Publication No. US20090081636.

Therapeutic vaccines useful in the present compositions and methods include, but are not limited to, IC41 (Intercell Novartis), CSL123 (Chiron/CSL), GI 5005 (Globeimmune), TG-4040 (Transgene), GNI-103 (GENimmune), Hepavaxx C (ViRex Medical), ChronVac-C (Inovio/Tripep), PeviPRO™ (Pevion Biotect), HCV/MF59 (Chiron/Novartis) and Civacir (NABI).

Examples of further additional therapeutic agents useful in the present compositions and methods include, but are not limited to, Ritonavir (Abbott), TT033 (Benitec/Tacere Bio/Pfizer), Sirna-034 (Sirna Therapeutics), GNI-104 (GENimmune), GI-5005 (GlobeImmune), IDX-102 (Idenix), Levovirin™ (ICN Pharmaceuticals, Costa Mesa, Calif.); Humax (Genmab), ITX-2155 (Ithrex/Novartis), PRO 206 (Progenics), HepaCide-I (NanoVirocides), MX3235 (Migenix), SCY-635 (Scynexis); KPE02003002 (Kemin Pharma), Lenocta (VioQuest Pharmaceuticals), IET—Interferon Enhancing Therapy (Transition Therapeutics), Zadaxin (SciClone Pharma), VP 50406™ (Viropharma, Incorporated, Exton, Pa.); Taribavirin (Valeant Pharmaceuticals); Nitazoxanide (Romark); Debio 025 (Debiopharm); GS-9450 (Gilead); PF-4878691 (Pfizer); ANA773 (Anadys); SCV-07 (SciClone Pharmaceuticals); NIM-881 (Novartis); ISIS 14803™ (ISIS Pharmaceuticals, Carlsbad, Calif.); Heptazyme™ (Ribozyme Pharmaceuticals, Boulder, Colo.); Thymosin™ (SciClone Pharmaceuticals, San Mateo, Calif.); Maxamine™ (Maxim Pharmaceuticals, San Diego, Calif.); NKB-122 (JenKen Bioscience Inc., North Carolina); Alinia (Romark Laboratories), INFORM-1 (a combination of R7128 and ITMN-191); and mycophenolate mofetil (Hoffman-LaRoche, Nutley, N.J.).

In one embodiment, when the additional therapeutic agent is INTRON-A interferon alpha 2b, which is administered by subcutaneous injection at 3MIU (12 mcg)/0.5 mL/TIW for 24 weeks or 48 weeks for first time treatment.

In another embodiment, when the additional therapeutic agent is PEG-INTRON interferon alpha 2b pegylated (commercially available from Schering-Plough Corp.), this agent is administered by subcutaneous injection at 1.5 mcg/kg/week, within a range of 40 to 150 mcg/week, for at least 24 weeks.

In another embodiment, when the additional therapeutic agent is ROFERON A interferon alpha 2a (commercially available from Hoffmann-La Roche), this agent is administered by subcutaneous or intramuscular injection at 3MIU (11.1 mcg/mL)/TIW for at least 48 to 52 weeks, or alternatively 6MIU/TIW for 12 weeks followed by 3MIU/TIW for 36 weeks.

In still another embodiment, when the additional therapeutic agent is PEGASUS interferon alpha 2a pegylated (commercially available from Hoffmann-La Roche), this agent is administered by subcutaneous injection at 180 mcg/1 mL or 180 mcg/0.5 mL, once a week for at least 24 weeks.

In yet another embodiment, when the additional therapeutic agent is INFERGEN interferon alphacon-1 (commercially available from Amgen), this agent is administered by subcutaneous injection at 9 mcg/TIW is 24 weeks for first time treatment and up to 15 mcg/TIW for 24 weeks for non-responsive or relapse treatment.

In a further embodiment, when the additional therapeutic agent is Ribavirin (commercially available as REBETOL ribavirin from Schering-Plough or COPEGUS ribavirin from Hoffmann-La Roche), this agent is administered at a daily dosage of from about 600 to about 1400 mg/day for at least 24 weeks.

In one embodiment, Compound A is administered with one or more additional therapeutic agents selected from: an interferon, an immunomodulator, a viral replication inhibitor, an antisense agent, a therapeutic vaccine, a viral polymerase inhibitor, a nucleoside inhibitor, a viral protease inhibitor, a viral helicase inhibitor, a viral polymerase inhibitor a virion production inhibitor, a viral entry inhibitor, a viral assembly inhibitor, an antibody therapy (monoclonal or polyclonal), and any agent useful for treating an RNA-dependent polymerase-related disorder.

In another embodiment, Compound A is administered with one or more additional therapeutic agents selected from an HCV protease inhibitor, an HCV polymerase inhibitor, an HCV replication inhibitor, a nucleoside, an interferon, a pegylated interferon and ribavirin. The combination therapies can include any combination of these additional therapeutic agents.

In another embodiment, Compound A is administered with one additional therapeutic agent selected from an HCV protease inhibitor, an interferon, a pegylated interferon and ribavirin.

In still another embodiment, Compound A is administered with two additional therapeutic agents selected from an HCV protease inhibitor, an HCV replication inhibitor, a nucleoside, an interferon, a pegylated interferon and ribavirin.

In another embodiment, Compound A is administered with an HCV protease inhibitor and ribavirin. In another specific embodiment, Compound A is administered with a pegylated interferon and ribavirin.

In another embodiment, Compound A is administered with three additional therapeutic agents selected from an HCV protease inhibitor, an HCV replication inhibitor, a nucleoside, an interferon, a pegylated interferon and ribavirin.

In one embodiment, Compound A is administered with one or more additional therapeutic agents selected from an HCV polymerase inhibitor, a viral protease inhibitor, an interferon, and a viral replication inhibitor. In another embodiment, Compound A is administered with one or more additional therapeutic agents selected from an HCV polymerase inhibitor, a viral protease inhibitor, an interferon, and a viral replication inhibitor. In another embodiment, Compound A is administered with one or more additional therapeutic agents selected from an HCV polymerase inhibitor, a viral protease inhibitor, an interferon, and ribavirin.

In one embodiment, Compound A is administered with one additional therapeutic agent selected from an HCV polymerase inhibitor, a viral protease inhibitor, an interferon, and a viral replication inhibitor. In another embodiment, Compound A is administered with ribavirin.

In one embodiment, Compound A is administered with two additional therapeutic agents selected from an HCV polymerase inhibitor, a viral protease inhibitor, an interferon, and a viral replication inhibitor.

In another embodiment, Compound A is administered with ribavirin, interferon and another therapeutic agent.

In another embodiment, Compound A is administered with ribavirin, interferon and another therapeutic agent, wherein the additional therapeutic agent is selected from an HCV polymerase inhibitor, a viral protease inhibitor, and a viral replication inhibitor.

In still another embodiment, Compound A is administered with ribavirin, interferon and a viral protease inhibitor.

In another embodiment, Compound A is administered with ribavirin, interferon and an HCV protease inhibitor.

In another embodiment, Compound A is administered with ribavirin, interferon and boceprevir or telaprevir.

In a further embodiment, Compound A is administered with ribavirin, interferon and an HCV polymerase inhibitor.

In another embodiment, Compound A is administered with pegylated-interferon alpha and ribavirin.

Kits

In one aspect, the present invention provides a kit comprising a therapeutically effective amount of Compound A, or a pharmaceutically acceptable salt, solvate or ester of said compound and a pharmaceutically acceptable carrier, vehicle or diluent.

In another aspect the present invention provides a kit comprising an amount of Compound A, or a pharmaceutically acceptable salt, solvate or ester of said compound and an amount of at least one additional therapeutic agent listed above, wherein the amounts of the two or more active ingredients result in a desired therapeutic effect. In one embodiment, Compound A and the one or more additional therapeutic agents are provided in the same container. In one embodiment, Compound A and the one or more additional therapeutic agents are provided in separate containers.

EXAMPLES

General Methods

Solvents, reagents, and intermediates that are commercially available were used as received. Reagents and intermediates that are not commercially available were prepared in the manner as described below. $^1$H NMR spectra were obtained on a Bruker Avance 500 (500 MHz) and are reported as ppm downfield from Me$_4$Si with number of protons, multiplicities, and coupling constants in Hertz indicated parenthetically. Where LC/MS data are presented, analyses was performed using an Applied Biosystems API-100 mass spectrometer and Shimadzu SCL-10A LC column: Altech platinum C18, 3 micron, 33 mm×7 mm ID; gradient flow: 0 minutes-10% CH$_3$CN, 5 minutes-95% CH$_3$CN, 5-7 minutes-95% CH$_3$CN, 7 minutes-stop. The retention time and observed parent ion are given. Flash column chromatography was performed using pre-packed normal phase silica from Biotage, Inc. or bulk silica from Fisher Scientific. Unless otherwise indicated, column chromatography was performed using a gradient elution of hexanes/ethyl acetate, from 100% hexanes to 100% ethyl acetate.

The X-ray powder diffraction patterns disclosed herein were generated on a Philips Analytical X'Pert PRO X-ray Diffraction System with PW3040/60 console. A PW3373/00 ceramic Cu LEF X-ray tube K-Alpha radiation was used as the source.

Example 1

Preparation of Compound A

Compound A was prepared using methods described in U.S. Patent Publication No. US20120083483.

Example 2

Methanol Solvate (Methanolate) of Compound A

The ethanolate of Compound A (350 mg) was suspended in 1.75 mL of methanol. The resulting suspension was allowed to age at 50° C. for 1 hour. The solution was then cooled to 5° C. and allowed to age overnight at this temperature, then was isolated cold to provide crystalline Compound A crystalline methanol solvate.

An XRPD pattern of the isolated methanolate was obtained and is shown in FIG. 1. 2Θ values and the corresponding d-spacings include the following:

| 2-θ, ° | d-spacing, Å | Relative Intensity, % |
|---|---|---|
| 5.82 | 15.18 | 24 |
| 6.19 | 14.27 | 95 |
| 7.94 | 11.14 | 37 |
| 9.52 | 9.29 | 30 |
| 10.10 | 8.75 | 72 |
| 11.36 | 7.79 | 26 |
| 12.41 | 7.13 | 61 |
| 13.29 | 6.66 | 59 |
| 15.76 | 5.62 | 77 |
| 16.27 | 5.45 | 25 |
| 17.27 | 5.13 | 79 |
| 17.73 | 5.00 | 41 |
| 18.12 | 4.90 | 50 |
| 18.76 | 4.73 | 43 |
| 19.47 | 4.56 | 45 |
| 20.07 | 4.43 | 58 |
| 20.42 | 4.35 | 27 |
| 21.24 | 4.18 | 100 |
| 21.95 | 4.05 | 17 |
| 22.65 | 3.93 | 27 |
| 22.95 | 3.88 | 39 |
| 23.28 | 3.82 | 22 |
| 24.17 | 3.68 | 19 |
| 24.88 | 3.58 | 36 |
| 25.67 | 3.47 | 24 |
| 29.45 | 3.03 | 18 |

Example 3

Ethanol Solvate (Ethanolate) of Compound A

Compound A was suspended in ethanol overnight to provide the crystalline ethanol solvate of Compound A.

Figure 2:
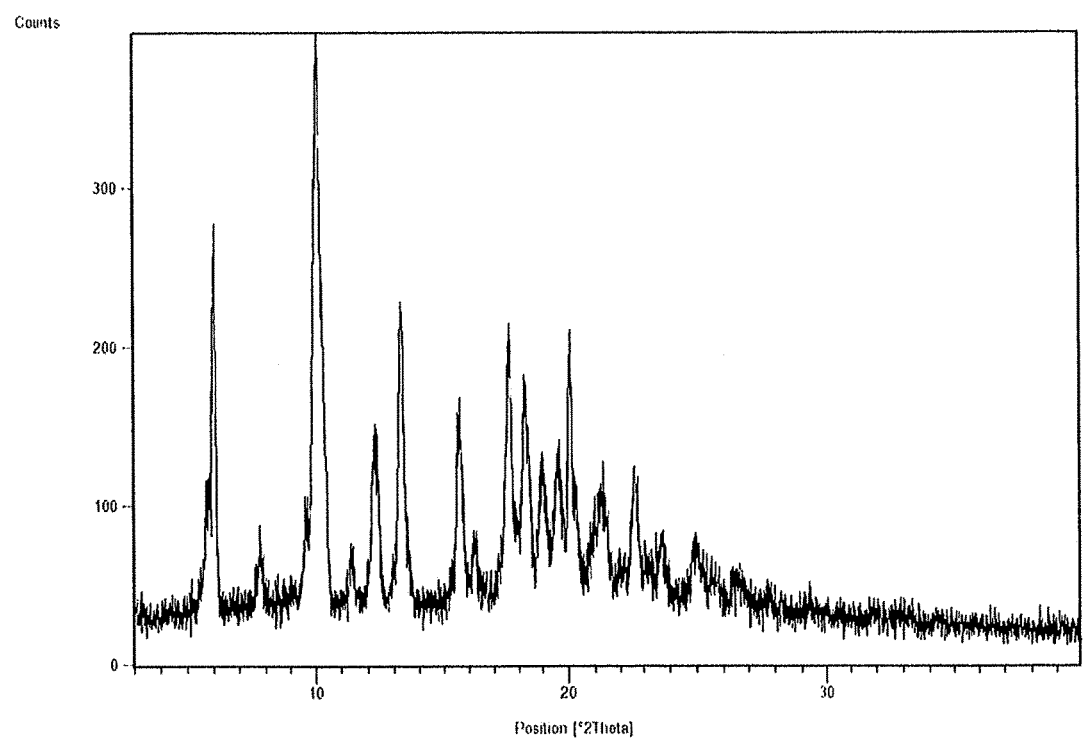
FIG. 2 shows the powder x-ray diffraction (XRPD) pattern of form B of Compound A (ethanolate).

An XRPD pattern of the isolated ethanolate was obtained and is shown in FIG. 2. 2Θ values and the corresponding d-spacings include the following:

| 2-θ, ° | d-spacing, Å | Relative Intensity, % |
|---|---|---|
| 6.13 | 14.42 | 73.4 |
| 7.86 | 11.24 | 15.8 |
| 9.59 | 9.22 | 14.6 |
| 10.05 | 8.80 | 100.0 |
| 11.42 | 7.75 | 9.8 |
| 12.37 | 7.16 | 35.8 |
| 13.30 | 6.66 | 59.2 |
| 13.67 | 6.48 | 9.4 |
| 15.66 | 5.66 | 47.5 |
| 16.23 | 5.46 | 15.1 |
| 17.53 | 5.06 | 51.4 |
| 17.93 | 4.95 | 15.2 |
| 18.28 | 4.85 | 42.6 |
| 18.94 | 4.69 | 30.3 |
| 19.58 | 4.53 | 36.1 |
| 20.06 | 4.43 | 34.3 |
| 20.93 | 4.24 | 15.5 |
| 21.27 | 4.18 | 29.1 |
| 22.70 | 3.92 | 28.5 |
| 23.25 | 3.83 | 10.2 |
| 23.67 | 3.76 | 14.1 |
| 24.85 | 3.58 | 18.5 |
| 25.67 | 3.47 | 8.5 |
| 26.20 | 3.40 | 7.2 |
| 26.91 | 3.31 | 7.0 |
| 27.76 | 3.21 | 4.5 |
| 29.20 | 3.06 | 4.4 |
| 29.84 | 2.99 | 2.6 |
| 30.45 | 2.94 | 2.7 |
| 31.72 | 2.82 | 3.5 |
| 32.94 | 2.72 | 4.6 |
| 35.85 | 2.50 | 0.8 |

Example 4

1-Propanol Solvate (1-Propanolate) of Compound A 386 mg of Compound A (ethanol solvate) were suspended in 1.93 mL of methanol. Mixture aged at 50° C. for 1 hour and cooled to 5° C. followed by two days aging at 5° C., then isolated cold to provide the crystalline 1-propanol solvate of Compound A.

Figure 3:
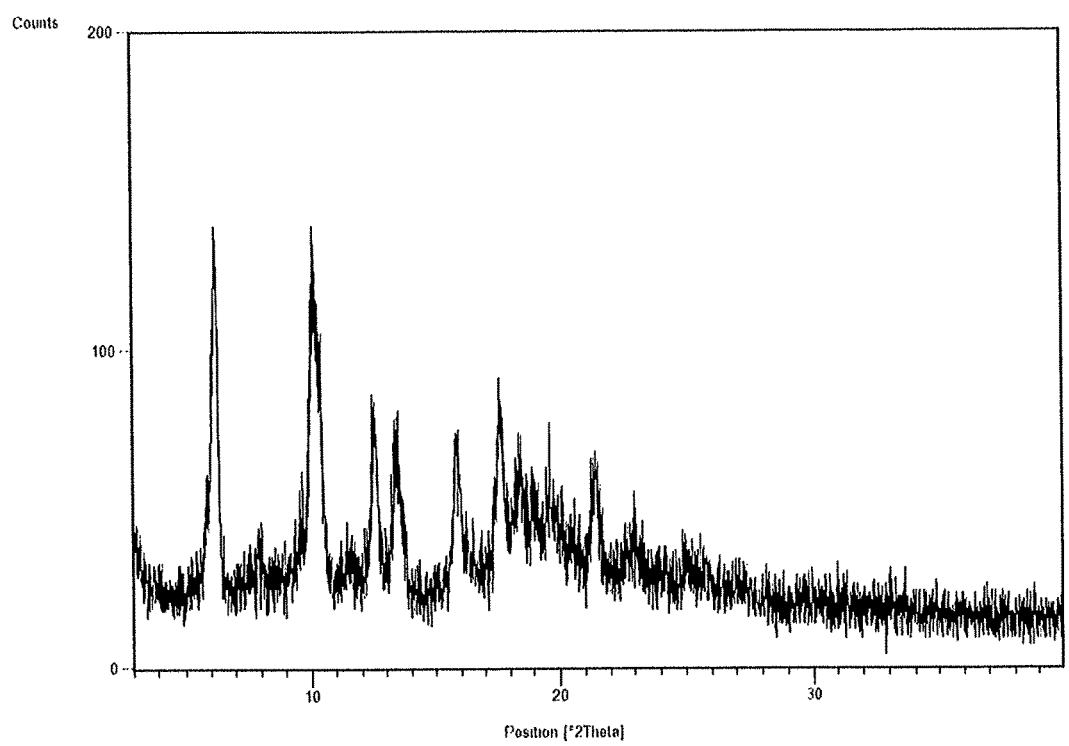
FIG. 3 shows the powder x-ray diffraction (XRPD) pattern of form C of Compound A (1-propanolate).

An XRPD pattern of the isolated 1-propanolate was obtained and is shown in FIG. 3. 2Θ values and the corresponding d-spacings include the following:

| 2-θ, ° | d-spacing, Å | Relative Intensity, % |
|---|---|---|
| 6.23 | 14.19 | 95 |
| 7.97 | 11.10 | 22 |
| 10.16 | 8.71 | 100 |
| 12.49 | 7.09 | 60 |
| 13.39 | 6.61 | 41 |
| 14.60 | 6.07 | 1 |
| 15.88 | 5.58 | 48 |
| 16.77 | 5.29 | 19 |
| 17.58 | 5.04 | 60 |
| 18.37 | 4.83 | 44 |
| 19.62 | 4.53 | 56 |
| 20.67 | 4.30 | 21 |
| 21.39 | 4.15 | 44 |
| 22.93 | 3.88 | 22 |
| 28.84 | 3.10 | 1 |

Example 5

2-Propanol Solvate (2-Propanolate) of Compound A 374 mg of Compound A (ethanol solvate) were suspended in 1.87 mL of methanol. Mixture aged at 50° C. for 1 hour and cooled to 5° C. followed by two days aging at 5° C., then isolated cold to provide to provide the crystalline 2-propanol solvate of Compound A.

Figure 4:
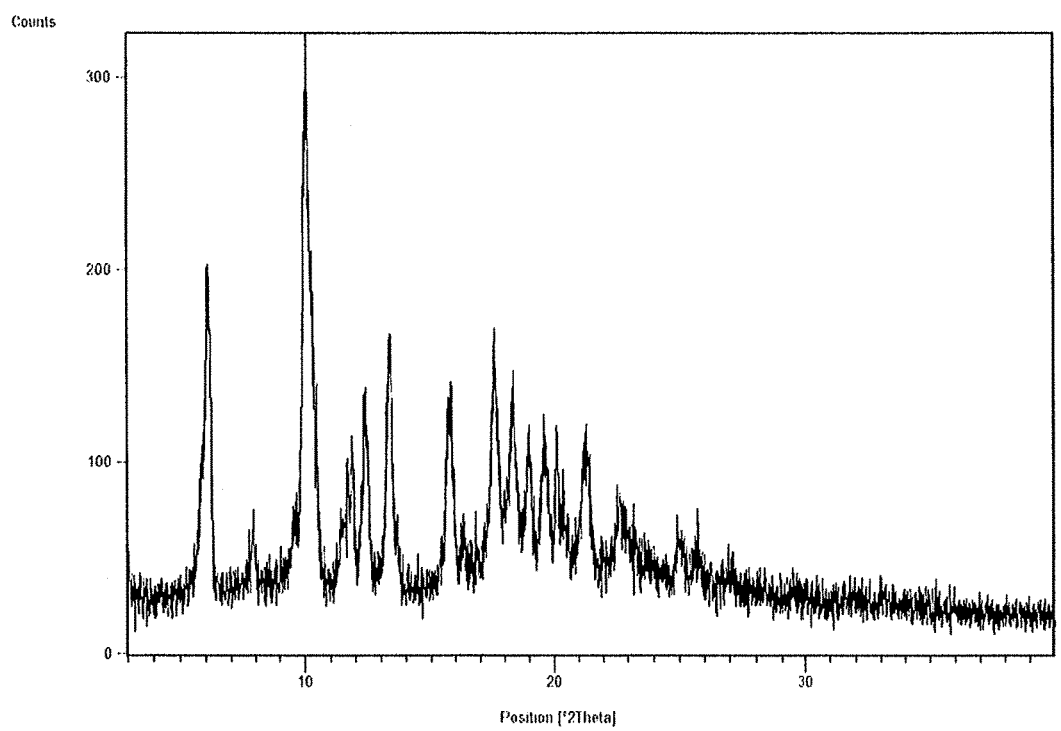
FIG. 4 shows the powder x-ray diffraction (XRPD) pattern of form D of Compound A (2-propanolate).

An XRPD pattern of the isolated 2-propanolate was obtained and is shown in FIG. 4. 2Θ values and the corresponding d-spacings include the following:

| 2-θ, ° | d-spacing, Å | Relative Intensity, % |
|---|---|---|
| 6.12 | 14.44 | 71 |
| 7.91 | 11.18 | 17 |
| 10.03 | 8.82 | 100 |
| 11.87 | 7.46 | 34 |
| 12.36 | 7.16 | 42 |
| 13.38 | 6.62 | 59 |
| 15.76 | 5.62 | 41 |
| 16.31 | 5.43 | 15 |
| 17.57 | 5.05 | 57 |
| 18.33 | 4.84 | 51 |
| 18.98 | 4.68 | 36 |
| 19.63 | 4.52 | 31 |
| 20.14 | 4.41 | 38 |
| 20.38 | 4.36 | 25 |
| 21.25 | 4.18 | 38 |
| 22.67 | 3.92 | 26 |
| 25.00 | 3.56 | 16 |

Example 6

Acetone Solvate (Acetonate) of Compound A 3.0 g of Compound A (amorphous) were dissolved in a mixture of acetone (5.5 g) and water (0.6 g). Acetone solvate seeds (0.1 g) were added and mixture was aged for 30 minutes. Additional water (2.4 g) was introduced and the batch was aged overnight to provide the crystalline acetone solvate of Compound A.

Figure 5:
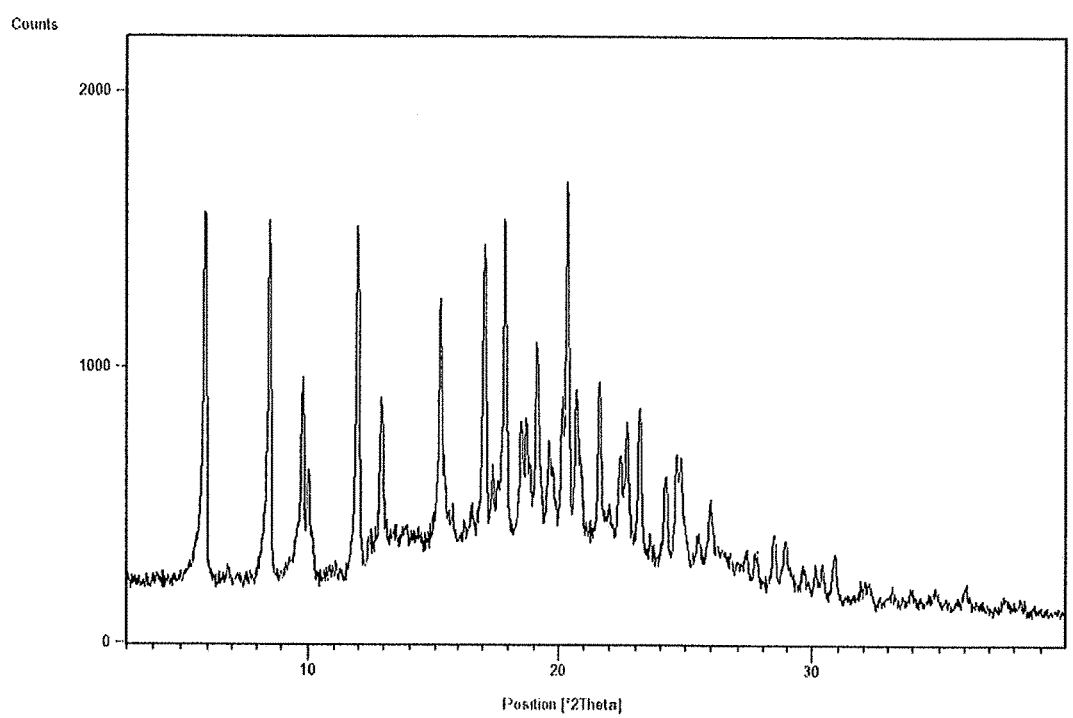
FIG. 5 shows the powder x-ray diffraction (XRPD) pattern of form E of Compound A (acetonate).

An XRPD pattern of the isolated acetonate was obtained and is shown in FIG. 5. 2Θ values and the corresponding d-spacings include the following:

| 2-θ, ° | d-spacing, Å | Relative Intensity, % |
|---|---|---|
| 5.92 | 14.94 | 91 |
| 8.52 | 10.38 | 94 |
| 9.78 | 9.05 | 55 |
| 9.98 | 8.86 | 32 |
| 11.97 | 7.40 | 95 |
| 12.94 | 6.84 | 50 |
| 15.22 | 5.82 | 71 |
| 17.07 | 5.19 | 90 |
| 17.89 | 4.96 | 90 |
| 18.51 | 4.79 | 44 |
| 18.69 | 4.75 | 45 |
| 19.13 | 4.64 | 61 |
| 19.62 | 4.52 | 39 |
| 20.39 | 4.36 | 100 |
| 20.75 | 4.28 | 51 |
| 21.66 | 4.10 | 53 |
| 22.42 | 3.97 | 36 |
| 22.66 | 3.92 | 44 |
| 23.16 | 3.84 | 48 |
| 24.19 | 3.68 | 31 |
| 24.67 | 3.61 | 36 |
| 24.82 | 3.59 | 35 |
| 25.99 | 3.43 | 24 |
| 28.46 | 3.14 | 17 |
| 28.91 | 3.09 | 15 |
| 30.85 | 2.90 | 11 |

Example 7

1-Butanol Solvate (1-Butanolate) of Compound A 210 mg of Compound A (ethanol solvate) was dissolved in 0.5 mL of 1-butanol and the solution was heated to 75° C. and allowed to age at this temperature for three days to provide the crystalline 1-butanol solvate of Compound A.

Figure 6:
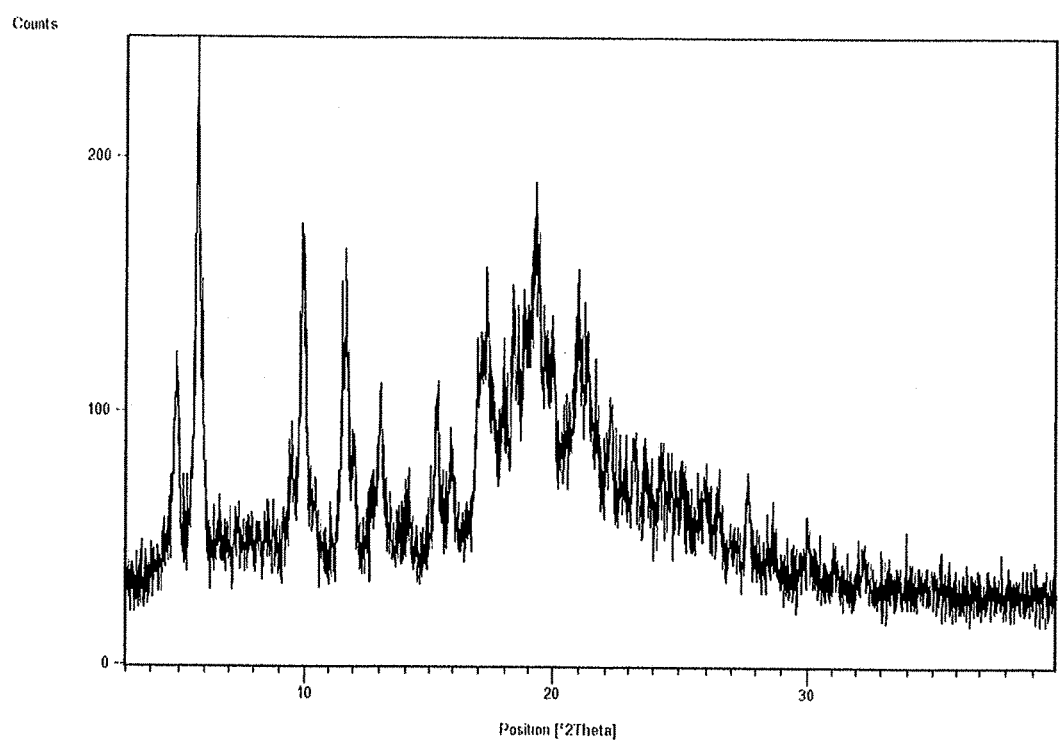
FIG. 6 shows the powder x-ray diffraction (XRPD) pattern of form F of Compound A (1-butanolate).

An XRPD pattern of the isolated 1-butanolate was obtained and is shown in FIG. 6. 2Θ values and the corresponding d-spacings include the following:

| 2-θ, ° | d-spacing, Å | Relative Intensity, % |
|---|---|---|
| 4.91 | 18.01 | 39 |
| 5.68 | 15.56 | 100 |
| 9.88 | 8.95 | 64 |
| 11.69 | 7.57 | 58 |
| 12.01 | 7.37 | 24 |
| 13.03 | 6.79 | 35 |
| 14.10 | 6.28 | 18 |
| 15.32 | 5.78 | 35 |
| 15.95 | 5.56 | 26 |
| 17.33 | 5.12 | 48 |
| 18.38 | 4.83 | 52 |
| 19.29 | 4.60 | 67 |
| 19.98 | 4.44 | 42 |
| 21.04 | 4.22 | 44 |
| 22.23 | 4.00 | 35 |
| 23.19 | 3.84 | 28 |
| 27.68 | 3.22 | 20 |

Example 8

Ethylene Glycol Solvate (Ethylene Glycolate) of Compound A 218 mg of Compound A (ethanol solvate) was dissolved in 0.2 mL of ethylene glycol and the resulting solution was heated to reflux for 10 minutes. The resulting solution was cooled to 75° C. and was allowed to age at this temperature for about 15 hours to provide the provided crystalline ethylene glycol solvate of Compound A.

Figure 7:
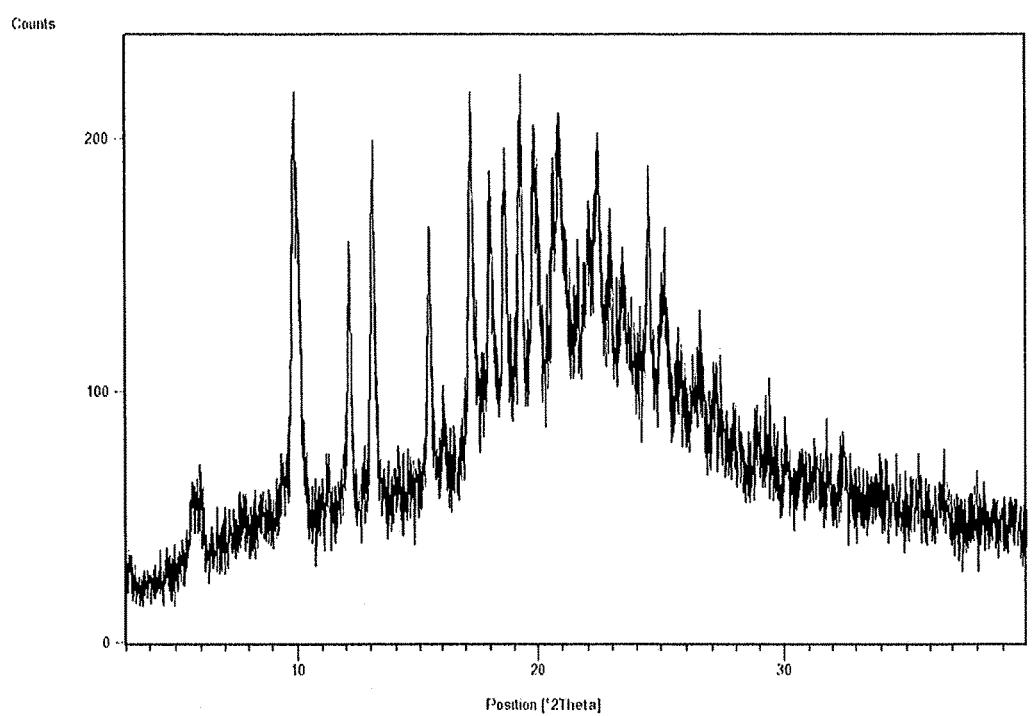
FIG. 7 shows the powder x-ray diffraction (XRPD) pattern of form G of Compound A (ethylene glycolate).

An XRPD pattern of the isolated ethylene glycolate was obtained and is shown in FIG. 7. 2Θ values and the corresponding d-spacings include the following:

| 2-θ, ° | d-spacing, Å | Relative Intensity, % |
|---|---|---|
| 5.90 | 14.99 | 13 |
| 9.00 | 9.82 | 15 |
| 9.87 | 8.96 | 98 |
| 11.18 | 7.92 | 21 |
| 12.16 | 7.28 | 63 |
| 13.08 | 6.77 | 84 |
| 15.43 | 5.74 | 66 |
| 16.03 | 5.53 | 32 |
| 17.23 | 5.15 | 100 |
| 18.06 | 4.91 | 72 |
| 18.58 | 4.78 | 77 |
| 19.30 | 4.60 | 88 |
| 19.86 | 4.47 | 90 |
| 20.93 | 4.24 | 95 |
| 22.42 | 3.96 | 89 |
| 22.99 | 3.87 | 66 |
| 23.48 | 3.79 | 59 |
| 24.53 | 3.63 | 85 |
| 25.15 | 3.54 | 55 |
| 26.62 | 3.35 | 41 |

Example 9

Propylene Glycol Solvate (Propylene Glycolate) of Compound A 12.5 g of Compound A (amorphous) was dissolved in 125 mL of an acetone-propylene glycol (19:1, v/v) mixture. The resulting solution was heated to 40° C. and propylene glycol solvate seeds were introduced. The resulting mixture was allowed to age for 30 minutes at 40° C., then allowed to cool to room temperature on its own to provide the crystalline propylene glycol solvate of Compound A.

Figure 8:
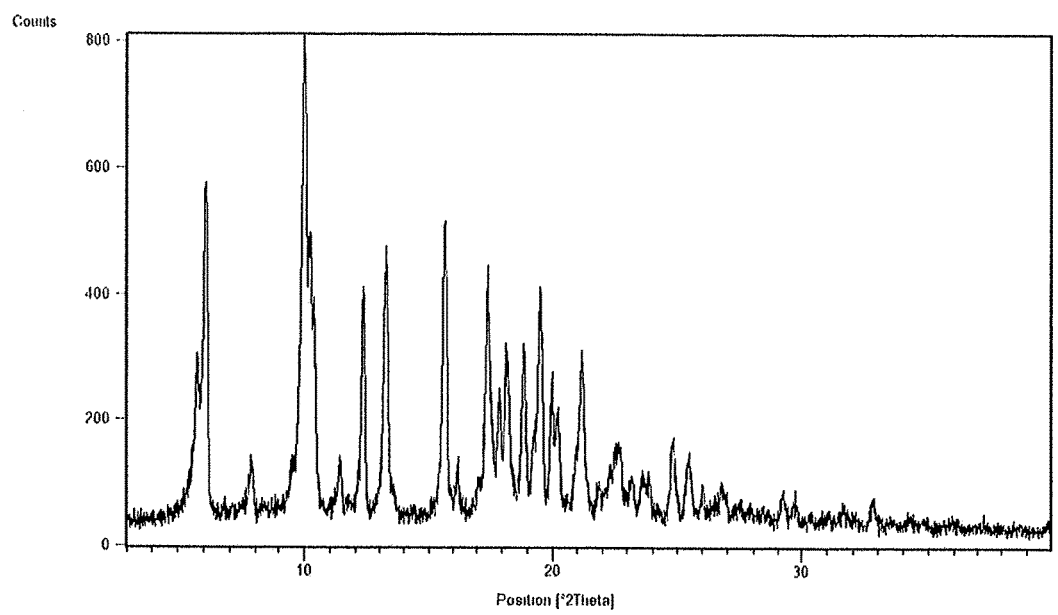
FIG. 8 shows the powder x-ray diffraction (XRPD) pattern of form H of Compound A (propylene glycolate).

An XRPD pattern of the isolated propylene glycolate was obtained and is shown in FIG. 8. 2Θ values and the corresponding d-spacings include the following:

| 2-θ, ° | d-spacing, Å | Relative Intensity, % |
|---|---|---|
| 5.78 | 15.28 | 35 |
| 6.08 | 14.53 | 71 |
| 7.87 | 11.24 | 12 |
| 9.99 | 8.85 | 100 |
| 10.19 | 8.68 | 61 |
| 10.35 | 8.55 | 47 |
| 11.36 | 7.79 | 12 |
| 12.32 | 7.18 | 50 |
| 13.28 | 6.67 | 57 |
| 15.64 | 5.66 | 63 |
| 16.15 | 5.49 | 11 |
| 17.43 | 5.09 | 49 |
| 17.90 | 4.96 | 29 |
| 18.20 | 4.87 | 36 |
| 18.88 | 4.70 | 38 |
| 19.52 | 4.55 | 46 |
| 19.99 | 4.44 | 33 |
| 20.19 | 4.40 | 22 |
| 21.20 | 4.19 | 36 |
| 21.88 | 4.06 | 9 |
| 22.62 | 3.93 | 15 |
| 23.17 | 3.84 | 10 |
| 23.59 | 3.77 | 12 |
| 24.79 | 3.59 | 18 |
| 25.45 | 3.50 | 14 |
| 26.03 | 3.42 | 9 |
| 26.83 | 3.32 | 7 |
| 29.23 | 3.06 | 7 |
| 29.71 | 3.01 | 5 |

Example 10

Methyl Isobutyl Ketone/Propylene Glycol Mixed Solvate of Compound A 1.70 g of Compound A was dissolved in 9 mL of ethyl acetate. The solution was solvent switched to methyl isobutyl ketone (9.5 mL), then the solution was heated to 50° C. and 6.9 mg of propylene glycol solvate seeds suspended in propylene glycol was added. The resulting mixture was mildly agitated at 50° C. and 0.224 g of propylene glycol was added slowly over 5 hours, while maintaining solution temperature at 50° C. During the addition of propylene glycol, solids precipitated and were isolated via filtration to provide the methyl isobutyl ketone-propylene glycol mixed solvate of Compound A.

Figure 9:
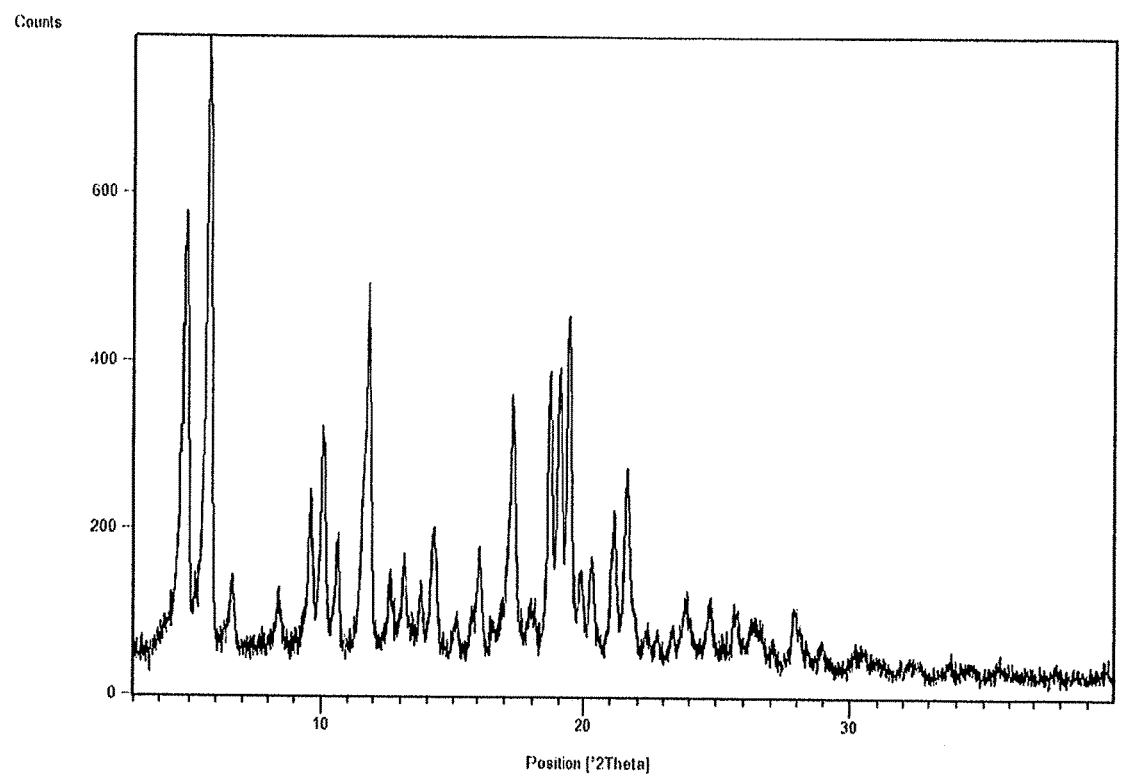
FIG. 9 shows the powder x-ray diffraction (XRPD) pattern of form I of Compound A (methyl isobutyl ketone/propylene glycol mixed solvate).
Figure 10:
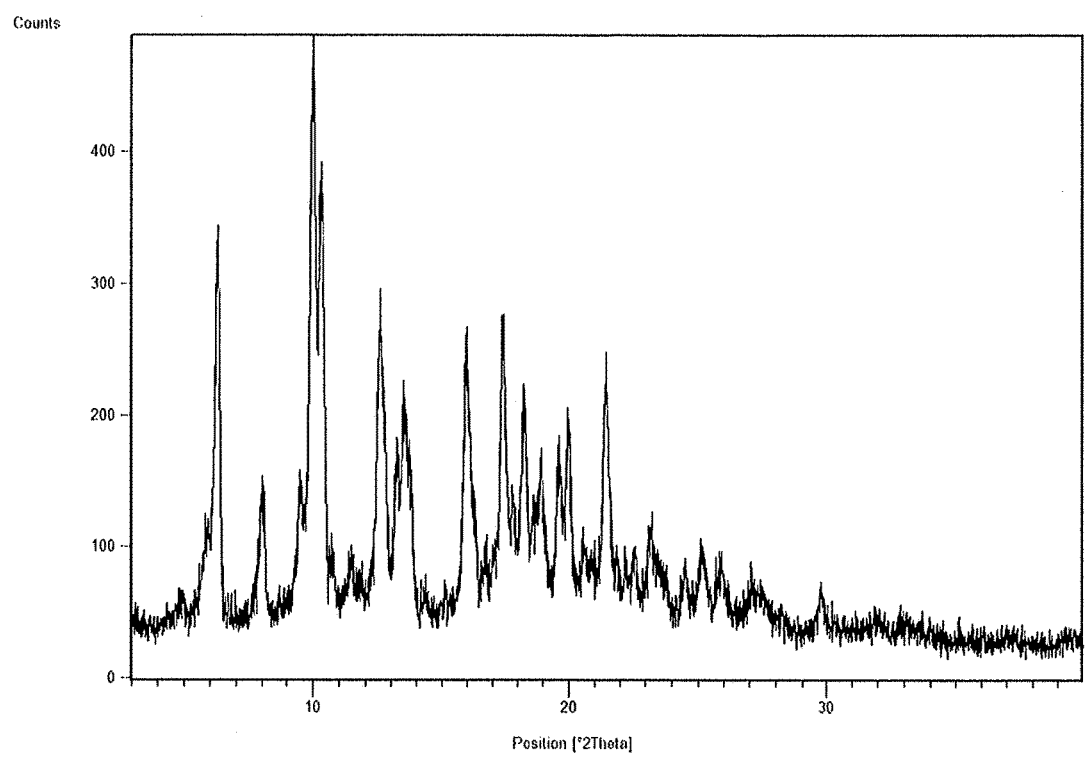
FIG. 10 shows the powder x-ray diffraction (XRPD) pattern of form J of Compound A (hydrate).

An XRPD pattern of the isolated methyl isobutyl ketone/propylene glycol mixed solvate was obtained and is shown in FIG. 9. 2Θ values and the corresponding d-spacings include the following:

| 2-θ, ° | d-spacing, Å | Relative Intensity, % |
|---|---|---|
| 4.89 | 18.08 | 73 |
| 5.74 | 15.41 | 100 |
| 6.63 | 13.33 | 13 |
| 8.42 | 10.50 | 12 |
| 9.61 | 9.20 | 26 |
| 10.07 | 8.78 | 37 |
| 10.59 | 8.36 | 20 |
| 11.82 | 7.49 | 58 |
| 12.64 | 7.00 | 15 |
| 13.14 | 6.74 | 41 |
| 13.75 | 6.44 | 16 |
| 14.31 | 6.19 | 20 |
| 15.16 | 5.85 | 10 |
| 16.06 | 5.52 | 21 |
| 16.58 | 5.35 | 7 |
| 17.28 | 5.13 | 45 |
| 17.93 | 4.95 | 11 |
| 18.66 | 4.75 | 49 |
| 19.03 | 4.66 | 48 |
| 19.42 | 4.57 | 57 |
| 19.92 | 4.46 | 15 |
| 20.36 | 4.36 | 22 |
| 21.18 | 4.20 | 25 |
| 21.61 | 4.11 | 31 |
| 22.34 | 3.98 | 6 |
| 22.76 | 3.91 | 7 |
| 23.34 | 3.81 | 7 |
| 23.87 | 3.73 | 12 |
| 24.76 | 3.60 | 11 |
| 25.72 | 3.46 | 10 |
| 26.33 | 3.39 | 7 |
| 27.89 | 3.20 | 10 |
| 28.98 | 3.08 | 6 |

Example 11

Amorphous Form of Compound A

The ethanolate of Compound A (1.0 g) was dissolved in 10 mL of ethyl acetate at 50° C. The resulting solution was added to 30 mL of heptane at 20° C. over 90 minutes. During the addition, solids precipitated as the amorphous form of Compound A.

Example 12

Hydrate of Compound A

The ethanolate of Compound A was exposed to elevated humidities at room temperature for several days by placing a glass vial containing a powder sample of Compound A in a glass dessicator containing water. The water and powder were not in contact, and water vapor substitution occurred in a closed system to provide crystalline hydrate of Compound A.

Figure 11:
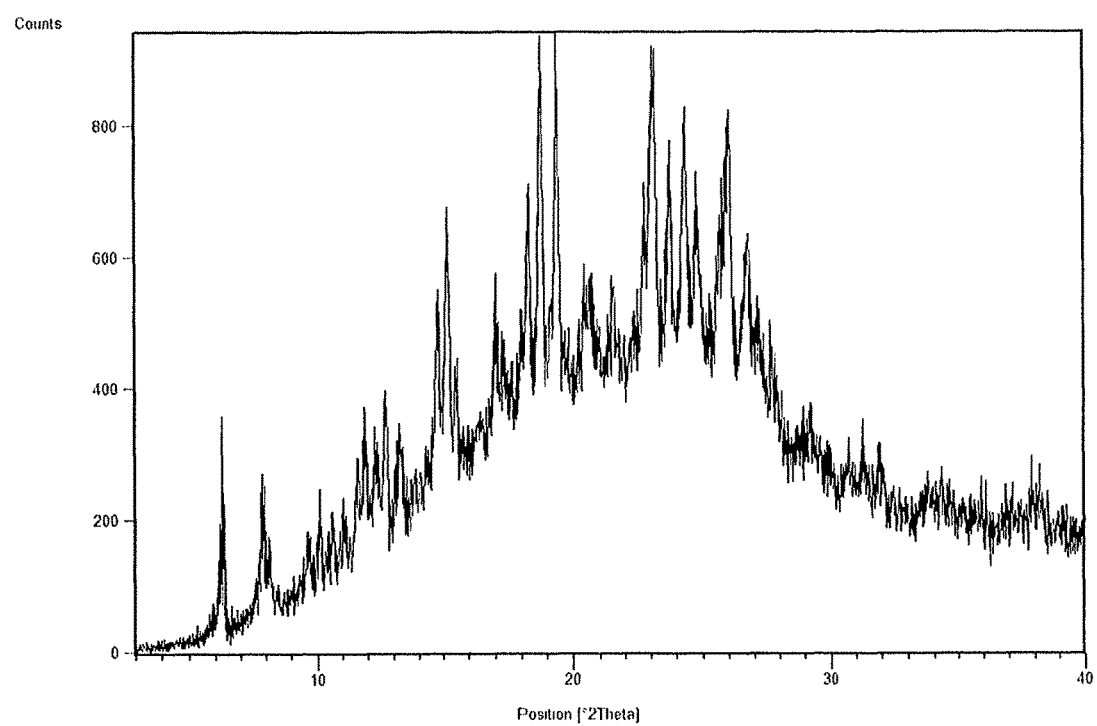
FIG. 11 shows the powder x-ray diffraction (XRPD) pattern of form K of Compound A (1,5-Napthalene Disulfonic Acid Salt Methanol Solvate).

An XRPD pattern of the isolated hydrate was obtained and is shown in FIG. 11. 2Θ values and the corresponding d-spacings include the following:

| 2-θ, ° | d-spacing, Å | Relative Intensity, % |
|---|---|---|
| 4.95 | 17.85 | 10 |
| 5.87 | 15.05 | 18 |
| 6.31 | 14.01 | 70 |
| 7.98 | 11.09 | 28 |
| 9.50 | 9.31 | 29 |
| 10.01 | 8.84 | 100 |
| 10.34 | 8.56 | 81 |
| 10.71 | 8.26 | 17 |
| 11.46 | 7.72 | 16 |
| 12.54 | 7.06 | 54 |
| 13.24 | 6.69 | 36 |
| 13.50 | 6.56 | 44 |
| 16.00 | 5.54 | 47 |
| 17.39 | 5.10 | 55 |

-continued

| 2-θ, ° | d-spacing, Å | Relative Intensity, % |
|---|---|---|
| 17.80 | 4.98 | 27 |
| 18.29 | 4.85 | 41 |
| 18.95 | 4.68 | 32 |
| 19.63 | 4.52 | 30 |
| 20.01 | 4.44 | 40 |
| 20.60 | 4.31 | 18 |
| 21.46 | 4.14 | 49 |
| 22.62 | 3.93 | 18 |
| 23.21 | 3.83 | 21 |
| 24.47 | 3.64 | 14 |
| 25.11 | 3.55 | 19 |
| 25.91 | 3.44 | 16 |

Example 13

1,5-Napthalene Disulfonic Acid Salt Methanol Solvate of Compound A

To a room temperature solution of Compound A (100 mg) in methanol (1 mL) was added 1,5-napthalene disulfonic acid tetrahydrate (1.0 eq., 40.83 mg). The resulting mixture was heated to 30° C. sonicated for 60 minutes in a Branson 5510 sonicator. The 1,5-napthalene disulfonic acid salt methanol solvate of Compound A precipitated as a solid during the sonication process.

Figure 12:
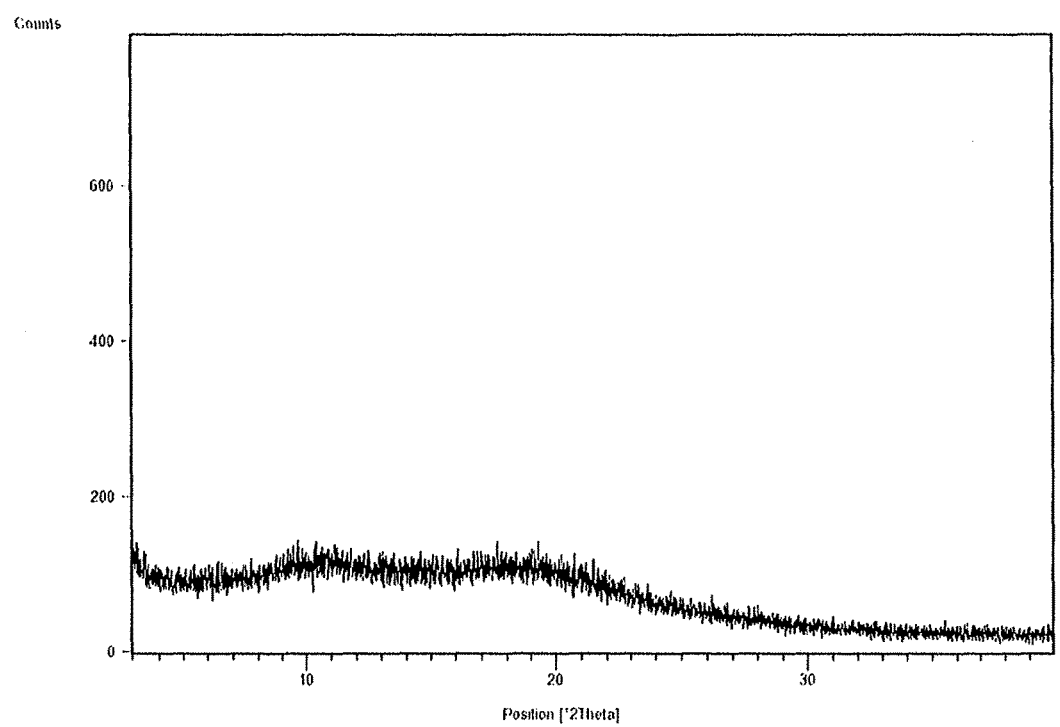
FIG. 12 shows the powder x-ray diffraction (XRPD) pattern of amorphous Compound A.

An XRPD pattern of the isolated 1,5-napthalene disulfonic acid salt methanol solvate was obtained and is shown in FIG. 12. 2Θ values and the corresponding d-spacings include the following:

| 2-θ, ° | d-spacing, Å | Relative Intensity, % |
|---|---|---|
| 6.29 | 14.06 | 20 |
| 7.90 | 11.20 | 22 |
| 9.64 | 9.17 | 12 |
| 10.07 | 8.78 | 19 |
| 11.61 | 7.62 | 22 |
| 11.89 | 7.44 | 34 |
| 12.31 | 7.19 | 31 |
| 12.70 | 6.97 | 34 |
| 13.26 | 6.68 | 29 |
| 14.78 | 5.99 | 52 |
| 15.16 | 5.84 | 64 |
| 15.51 | 5.71 | 41 |
| 17.04 | 5.20 | 55 |
| 18.27 | 4.85 | 72 |
| 18.77 | 4.73 | 99 |
| 19.43 | 4.57 | 100 |
| 20.68 | 4.29 | 53 |
| 21.54 | 4.12 | 55 |
| 23.11 | 3.85 | 94 |
| 23.75 | 3.75 | 81 |
| 24.34 | 3.66 | 84 |
| 24.77 | 3.59 | 75 |
| 26.02 | 3.42 | 82 |
| 26.75 | 3.33 | 63 |
| 31.28 | 2.86 | 32 |

What is claimed is:

1. A crystalline form of the compound having the structure:

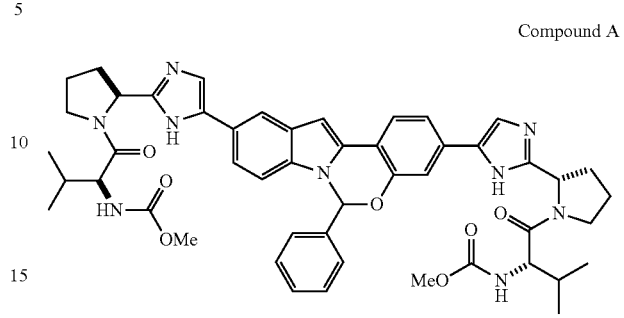

Compound A wherein said crystalline form is selected from the following forms: Form A (methanolate), Form B (ethanolate), Form C (1-propanolate), Form D (2-propanolate), Form E (acetonate), Form F (1-butanolate), Form G (ethylene glycolate), Form H (propylene glycolate), Form I (methyl isobutyl ketone/propylene glycol mixed solvate), Form J (hydrate) and Form K (1,5-naphthalene disulfonic acid salt).

2. The crystalline form according to claim 1, which is pharmaceutically acceptable.

3. The crystalline form of claim 1, which is the 1,5-napthalene disulfonic acid salt of Compound A.

4. A pharmaceutical composition comprising an effective amount of the crystalline form of claim 1 and a pharmaceutically acceptable carrier.

5. The pharmaceutical composition according to claim 4, further comprising a second therapeutic agent selected from the group consisting of HCV antiviral agents, immunomodulators, and anti-infective agents.

6. A pharmaceutical composition comprising:
(1) the crystalline form of claim 1;
(2) a concentration-enhancing polymer, where the concentration-enhancing polymer increases the bioavailability or enhances the dissolution behavior of the crystalline form of claim 1, and is water soluble or readily disperses in water; and
(3) optionally one or more surfactants.

7. The crystalline form of claim 1, which is Form A (methanolate), having an X-ray powder diffraction pattern comprising diffraction peaks at 2-theta values, when measured using Cu $K_\alpha$ radiation, of about 6.19±0.2, 10.10±0.2, 15.76±0.2, 17.27±0.2 and 21.24±0.2.

8. The crystalline form of claim 1, which is Form B (ethanolate), having an X-ray powder diffraction pattern comprising diffraction peaks at 2-theta values, when measured using Cu $K_\alpha$ radiation, of about 6.13±0.2, 10.05±0.2, 13.30±0.2, 15.66±0.2 and 17.53±0.2.

9. The crystalline form of claim 1, which is Form C (1-propanolate), having an X-ray powder diffraction pattern comprising diffraction peaks at 2-theta values, when measured using Cu $K_\alpha$ radiation, of about 6.23±0.2, 10.16±0.2, 12.49±0.2, 18.37±0.2 and 19.62±0.2.

10. The crystalline form of claim 1, which is Form D (2-propanolate), having an X-ray powder diffraction pattern comprising diffraction peaks at 2-theta values, when measured using Cu $K_\alpha$ radiation, of 6.12±0.2, 10.03±0.2, 13.38±0.2, 17.57±0.2 and 18.33±0.2.

11. The crystalline form of claim 1, which is Form E (acetonate), having an X-ray powder diffraction pattern comprising diffraction peaks at 2-theta values, when measured using Cu $K_\alpha$ radiation, of about 5.92±0.2, 8.52±0.2, 11.97±0.2, 17.07±0.2 and 20.39±0.2.

12. The crystalline form of claim 1, which is Form F (1-butanolate), having an X-ray powder diffraction pattern comprising diffraction peaks at 2-theta values, when measured using Cu $K_\alpha$ radiation, of about 5.68±0.2, 9.88±0.2, 11.69±0.2, 18.38±0.2 and 19.29±0.2.

13. The crystalline form of claim 1, which is Form G (ethylene glycolate), having an X-ray powder diffraction pattern comprising diffraction peaks at 2-theta values, when measured using Cu $K_\alpha$ radiation, of about 9.87±0.2, 13.08±0.2, 17.23±0.2, 19.86±0.2 and 20.93±0.2.

14. The crystalline form of claim 1, which is Form H (propylene glycolate), having an X-ray powder diffraction pattern comprising diffraction peaks at 2-theta values, when measured using Cu $K_\alpha$ radiation, of about 6.08±0.2, 9.99±0.2, 13.28±0.2, 15.64±0.2 and 17.43±0.2.

15. The crystalline form of claim 1, which is Form I (methyl isobutyl ketone/propylene glycol mixed solvate), having an X-ray powder diffraction pattern comprising diffraction peaks at 2-theta values, when measured using Cu $K_\alpha$ radiation, of about 4.89±0.2, 5.74±0.2, 11.82±0.2, 18.66±0.2 and 19.42±0.2.

16. The crystalline form of claim 1, which is Form J (hydrate), having an X-ray powder diffraction pattern comprising diffraction peaks at 2-theta values, when measured using Cu $K_\alpha$ radiation, of about 6.31±0.2, 10.01±0.2, 10.34±0.2, 12.54±0.2 and 17.39±0.2.

17. The crystalline form of claim 1, which is Form K (1,5-napthalene disulfonic acid salt), having an X-ray powder diffraction pattern comprising diffraction peaks at 2-theta values, when measured using Cu $K_\alpha$ radiation, of about 15.16±0.2, 18.77±0.2, 19.43±0.2, 23.11±0.2 and 24.34±0.2.

\* \* \* \* \*